(12) United States Patent
Sakaguchi

(10) Patent No.: US 10,896,530 B2
(45) Date of Patent: Jan. 19, 2021

(54) MEDICAL INFORMATION PROCESSING APPARATUS AND MEDICAL INFORMATION PROCESSING METHOD

(71) Applicant: CANON MEDICAL SYSTEMS CORPORATION, Otawara-shi (JP)

(72) Inventor: Takuya Sakaguchi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 15/724,793

(22) Filed: Oct. 4, 2017

(65) Prior Publication Data

US 2018/0092616 A1 Apr. 5, 2018

(30) Foreign Application Priority Data

Oct. 4, 2016 (JP) .................................. 2016-196802

(51) Int. Cl.
 *G06T 11/20* (2006.01)
 *A61B 6/00* (2006.01)
 (Continued)

(52) U.S. Cl.
 CPC ............ *G06T 11/206* (2013.01); *A61B 6/504* (2013.01); *G06T 7/0016* (2013.01); *G16H 30/40* (2018.01);
 (Continued)

(58) Field of Classification Search
 CPC ....... G06F 3/00; G06T 11/206; G06T 7/0016; G06T 2207/10081; G06T 2207/30104;
 (Continued)

(56) References Cited

U.S. PATENT DOCUMENTS

2012/0041318 A1 2/2012 Taylor
2012/0041319 A1 2/2012 Taylor et al.
(Continued)

FOREIGN PATENT DOCUMENTS

JP  63-73943     4/1988
JP  2013-534154  9/2013

OTHER PUBLICATIONS

Coenen, Adriaan, et al., "Fractional Flow Reserve Computed from Noninvasive CT Angiography Data: Diagnostic Performance of an On-Site Clinician-operated Computational Fluid Dynamics Algorithm", Radiology, vol. 274, No. 3, pp. 674-683 (Year: 2015).*

(Continued)

*Primary Examiner* — William A Beutel
(74) *Attorney, Agent, or Firm* — Oblon, McClelland, Maier & Neustadt, L.L.P.

(57) ABSTRACT

A medical information processing apparatus according to an embodiment includes processing circuitry. The processing circuitry acquires a first index value obtained based on fluid analysis that is performed based on an image including a blood vessel of a subject, the first index value being related to blood flow at each of positions in the blood vessel. The processing circuitry acquires external information including a second index value related to blood flow at each of the positions in the blood vessel. The processing circuitry changes one of an arrangement direction of index values in a first graph and an arrangement direction of index values in a second graph in accordance with the other one of the arrangement directions. The processing circuitry displays the first graph and the second graph on a display unit such that the arrangement directions of the index values match each other.

13 Claims, 14 Drawing Sheets

(51) Int. Cl.
*G16H 30/40* (2018.01)
*G06T 7/00* (2017.01)
*G16H 50/30* (2018.01)

(52) U.S. Cl.
CPC .............. *G16H 50/30* (2018.01); *A61B 6/56* (2013.01); *G06T 2207/10081* (2013.01); *G06T 2207/30104* (2013.01)

(58) Field of Classification Search
CPC ........ G16H 30/40; G16H 50/30; A61B 6/504; A61B 6/56; A61B 6/5217; A61B 6/032
See application file for complete search history.

(56) References Cited

U.S. PATENT DOCUMENTS

| | | |
|---|---|---|
| 2012/0041320 A1 | 2/2012 | Taylor |
| 2012/0041321 A1 | 2/2012 | Taylor et al. |
| 2012/0041322 A1 | 2/2012 | Taylor et al. |
| 2012/0041323 A1 | 2/2012 | Taylor et al. |
| 2012/0041324 A1 | 2/2012 | Taylor et al. |
| 2012/0041735 A1 | 2/2012 | Taylor |
| 2012/0041739 A1 | 2/2012 | Taylor |
| 2012/0053919 A1 | 3/2012 | Taylor |
| 2012/0053921 A1 | 3/2012 | Taylor |
| 2012/0059246 A1 | 3/2012 | Taylor |
| 2012/0150516 A1 | 6/2012 | Taylor et al. |
| 2013/0054214 A1 | 2/2013 | Taylor |
| 2013/0064438 A1 | 3/2013 | Taylor et al. |
| 2013/0066618 A1 | 3/2013 | Taylor et al. |
| 2013/0151163 A1 | 6/2013 | Taylor et al. |
| 2013/0211728 A1 | 8/2013 | Taylor et al. |
| 2014/0107935 A1 | 4/2014 | Taylor |
| 2014/0148693 A1 | 5/2014 | Taylor |
| 2014/0155770 A1 | 6/2014 | Taylor |
| 2014/0207432 A1 | 7/2014 | Taylor |
| 2014/0222406 A1 | 8/2014 | Taylor |
| 2014/0236492 A1 | 8/2014 | Taylor |
| 2014/0243663 A1 | 8/2014 | Taylor |
| 2014/0247970 A1 | 9/2014 | Taylor |
| 2014/0249791 A1 | 9/2014 | Taylor |
| 2014/0249792 A1 | 9/2014 | Taylor |
| 2014/0276139 A1* | 9/2014 | Burkett .............. A61B 5/02156 600/486 |
| 2014/0348412 A1 | 11/2014 | Taylor |
| 2014/0355859 A1 | 12/2014 | Taylor et al. |
| 2015/0073722 A1 | 3/2015 | Taylor et al. |
| 2015/0088015 A1 | 3/2015 | Taylor |
| 2015/0088478 A1 | 3/2015 | Taylor |
| 2015/0150530 A1 | 6/2015 | Taylor et al. |
| 2015/0161326 A1 | 6/2015 | Taylor et al. |
| 2015/0161348 A1 | 6/2015 | Taylor et al. |
| 2015/0201849 A1 | 7/2015 | Taylor |
| 2015/0262388 A1* | 9/2015 | Ishii ....................... A61B 6/465 382/131 |
| 2015/0313478 A1* | 11/2015 | Veszelei ............... A61B 5/0215 600/483 |
| 2015/0332015 A1 | 11/2015 | Taylor |
| 2015/0339459 A1 | 11/2015 | Taylor |
| 2015/0363941 A1 | 12/2015 | Taylor |
| 2015/0379230 A1 | 12/2015 | Taylor |
| 2016/0007945 A1 | 1/2016 | Taylor |
| 2016/0012621 A1* | 1/2016 | Kanada ................... G06F 3/048 345/440 |
| 2016/0073991 A1 | 3/2016 | Taylor |
| 2016/0110517 A1 | 4/2016 | Taylor |
| 2016/0110866 A1 | 4/2016 | Taylor |
| 2016/0110867 A1 | 4/2016 | Taylor |
| 2016/0113528 A1 | 4/2016 | Taylor |
| 2016/0113726 A1 | 4/2016 | Taylor |
| 2016/0117815 A1 | 4/2016 | Taylor |
| 2016/0117816 A1 | 4/2016 | Taylor |
| 2016/0117819 A1 | 4/2016 | Taylor |
| 2016/0128661 A1 | 5/2016 | Taylor |
| 2016/0133015 A1 | 5/2016 | Taylor |
| 2016/0135787 A1* | 5/2016 | Anderson .............. A61B 6/504 600/440 |
| 2016/0140313 A1 | 5/2016 | Taylor |
| 2016/0232667 A1 | 8/2016 | Taylor |
| 2016/0246939 A1 | 8/2016 | Taylor |
| 2016/0296287 A1 | 10/2016 | Taylor |
| 2016/0364859 A1 | 12/2016 | Taylor |
| 2016/0364860 A1 | 12/2016 | Taylor |
| 2016/0364861 A1 | 12/2016 | Taylor |
| 2016/0371455 A1 | 12/2016 | Taylor |
| 2017/0053092 A1 | 2/2017 | Taylor |
| 2017/0202621 A1 | 7/2017 | Taylor |

OTHER PUBLICATIONS

StackOverflow, "Matlab—reverse value of axis in plot [duplicate]", published at https://stackoverflow.com/questions/6429087/matlab-reverse-value-of-axis-in-plot, archived at archive.org (Year: 2013).*

* cited by examiner

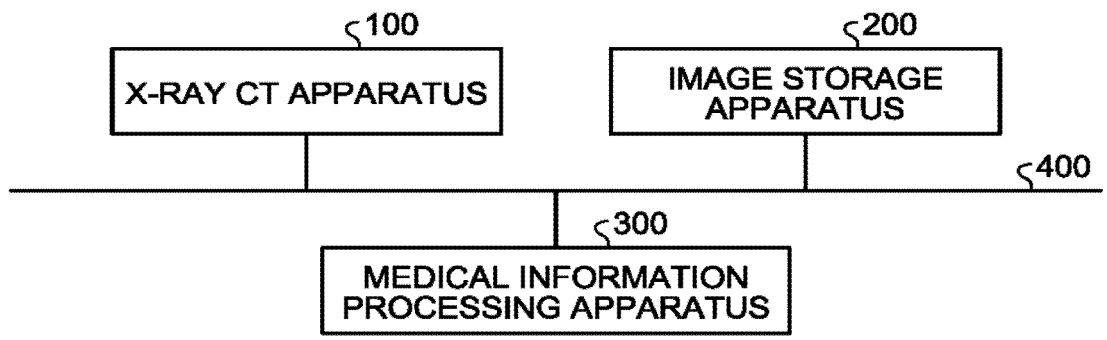
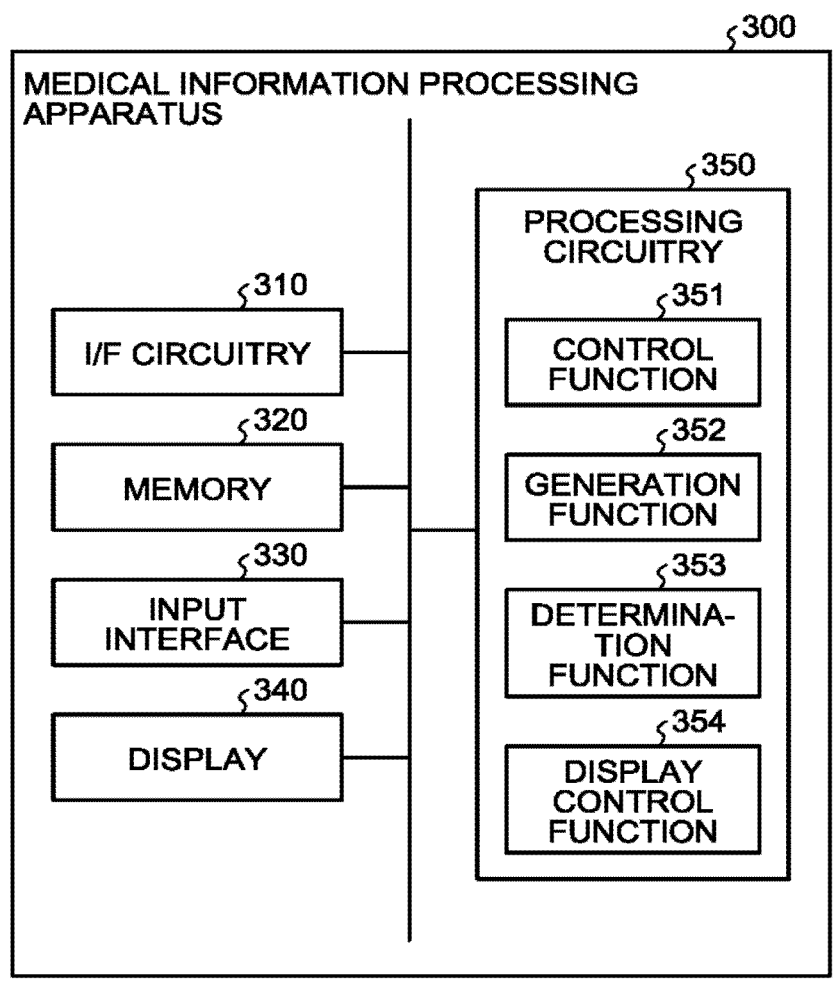

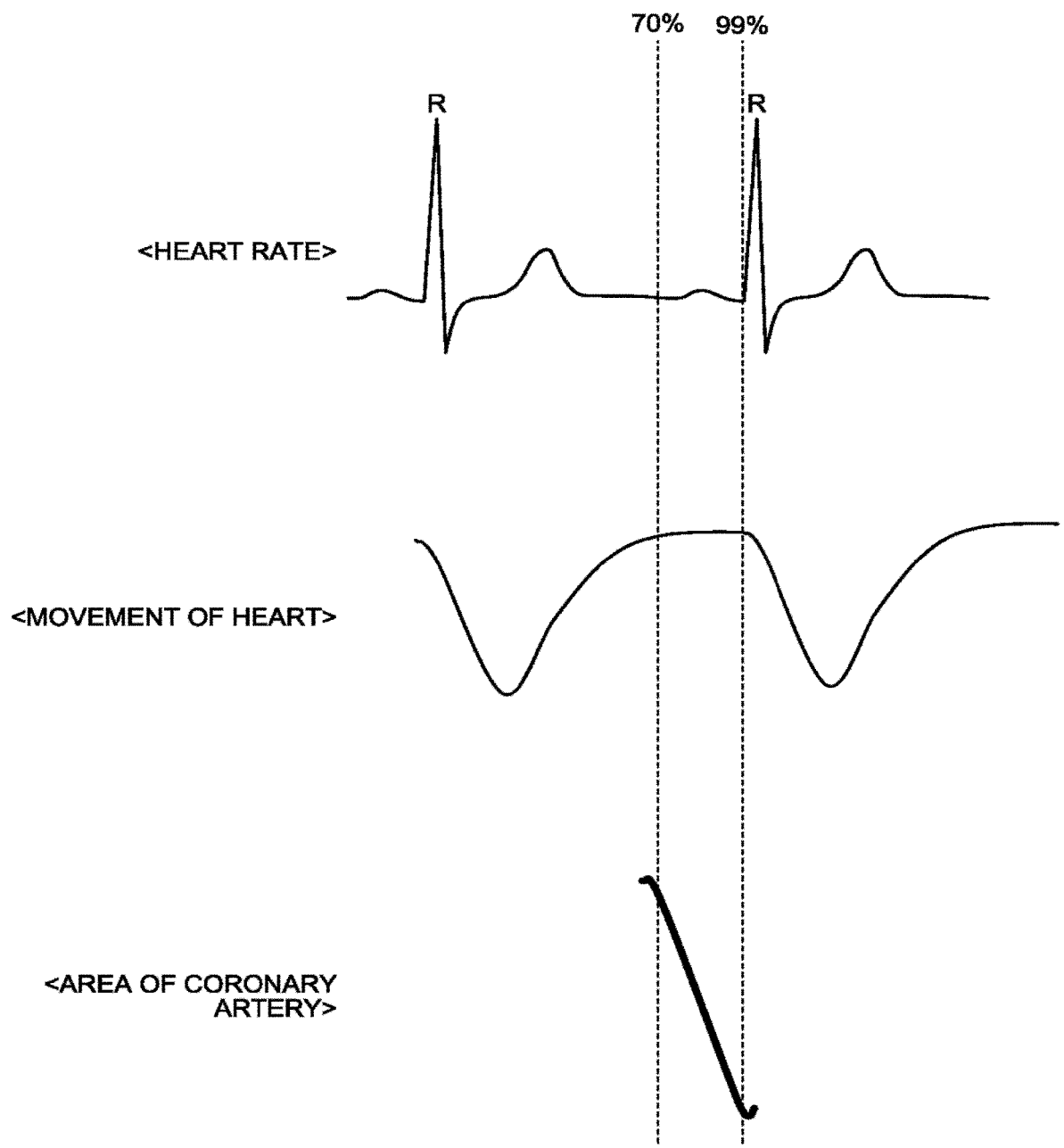

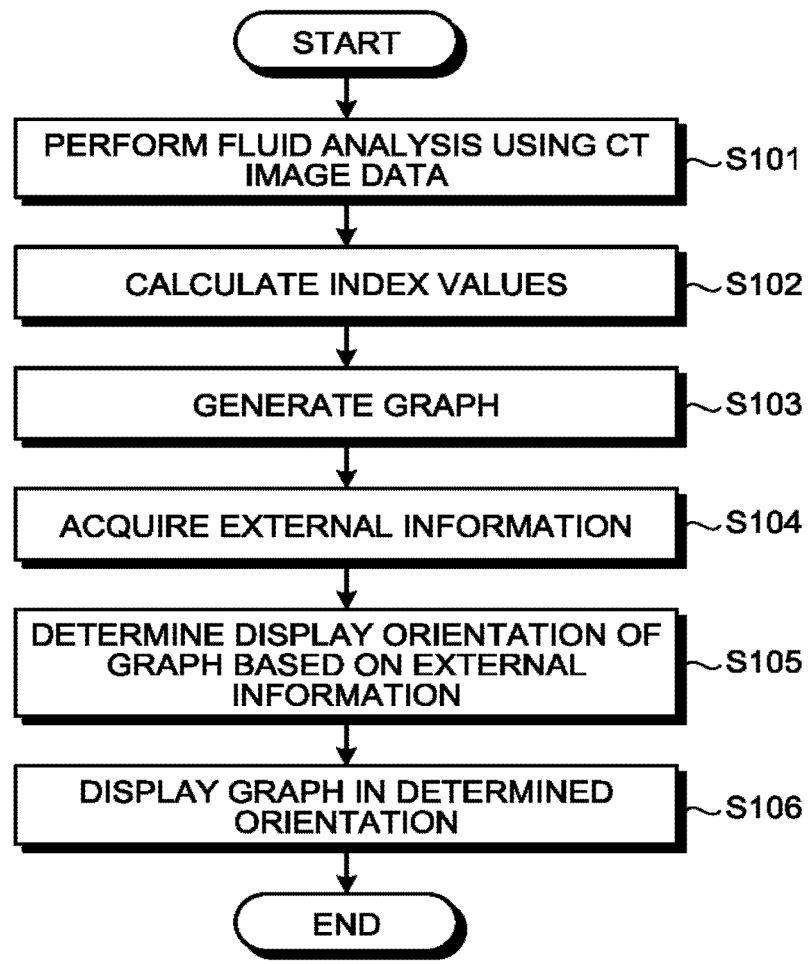

FIG.11A
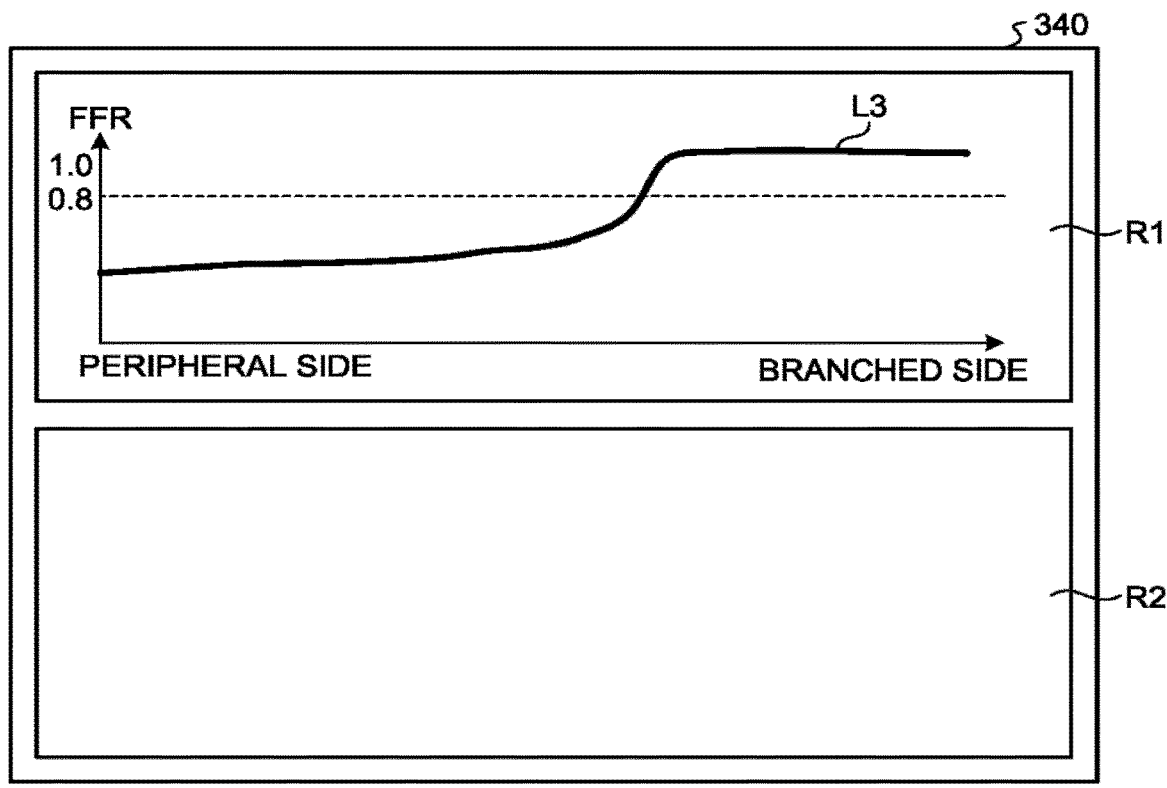
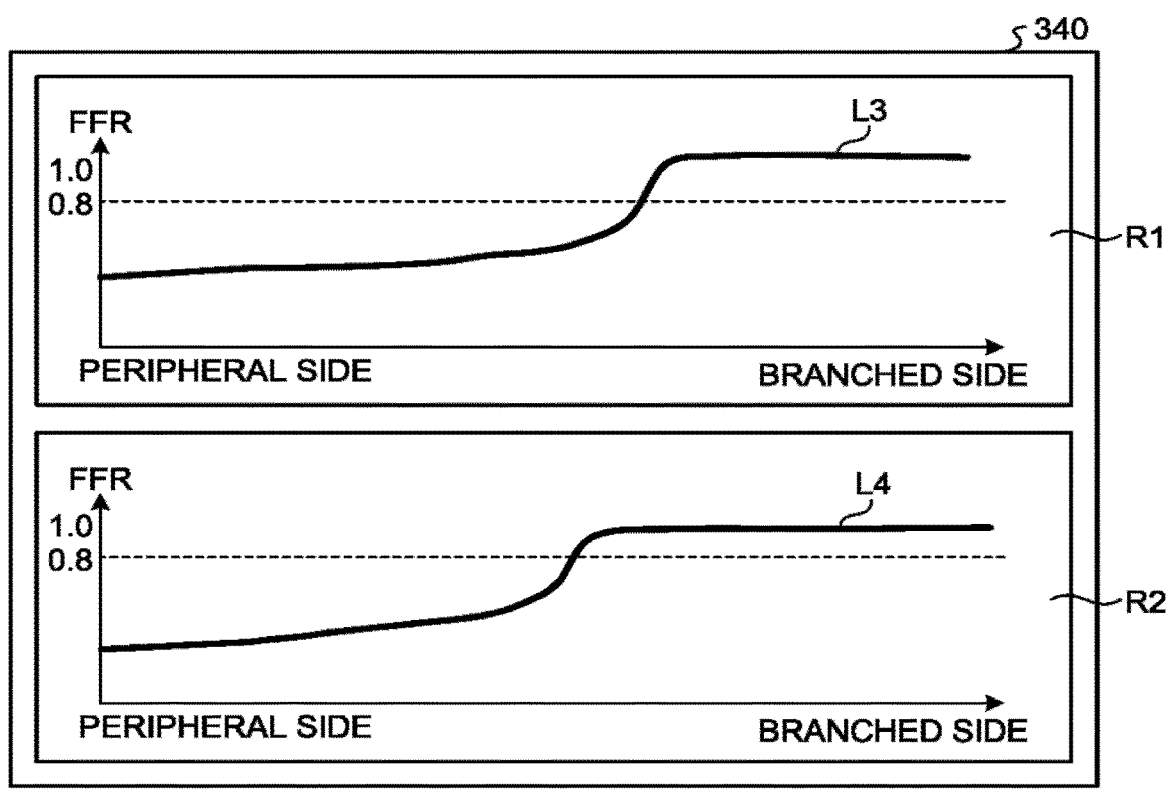

FIG.11B
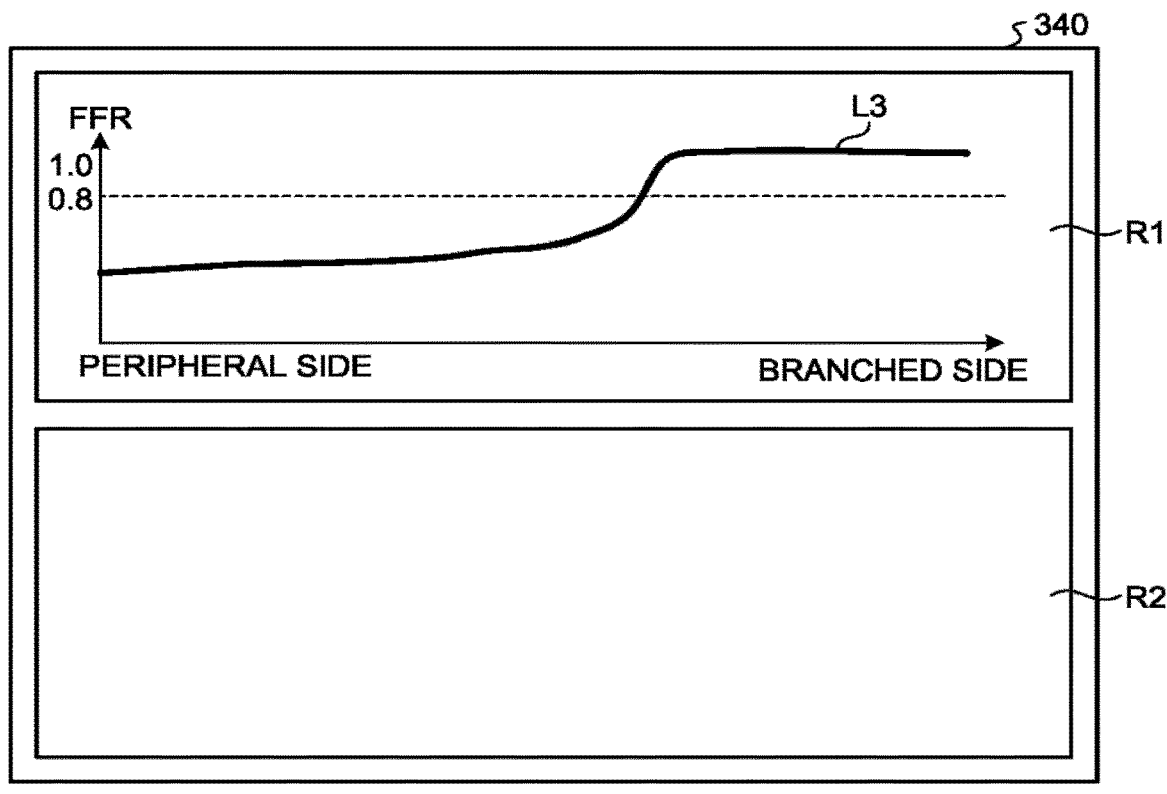
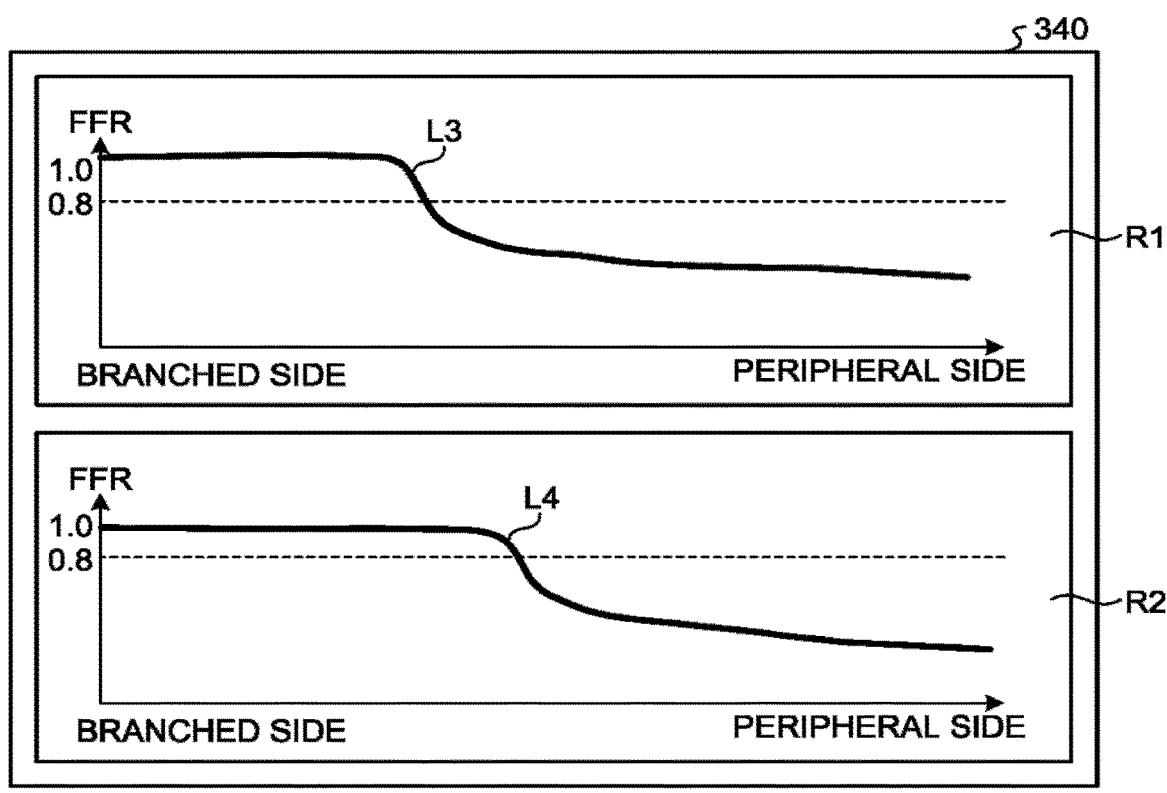

MEDICAL INFORMATION PROCESSING APPARATUS AND MEDICAL INFORMATION PROCESSING METHOD

CROSS-REFERENCE TO RELATED APPLICATIONS

This application is based upon and claims the benefit of priority from Japanese Patent Application No. 2016-196802, filed on Oct. 4, 2016; the entire contents of which are incorporated herein by reference.

FIELD

Embodiments described herein relate generally to a medical information processing apparatus and a medical information processing method.

BACKGROUND

It is conventionally known that the causes of ischemic diseases of organs are broadly divided into poor blood circulation and dysfunction of organs themselves. For example, a stenosis, which is an example of poor blood circulation of a coronary artery, is a serious lesion that causes ischemic heart diseases, and there is a need to determine whether to conduct drug treatment, stent treatment, or the like for the ischemic heart diseases. In recent years, as a diagnosis for performing evaluation of hematogenous ischemia in a coronary artery, there has been a recommended technique to measure myocardial fractional flow reserve (FFR) by using a pressure wire in coronary angiographic examination (coronary angiography: CAG) using a catheter.

Alternatively, there is a known technique to non-invasively perform evaluation of hematogenous ischemia in a coronary artery by using medical images of a heart, which are collected by, for example, a medical image diagnostic apparatus, such as an X-ray computer tomography (CT) apparatus, a magnetic, resonance imaging (MRI) apparatus, or an ultrasonic diagnostic apparatus. In this manner, evaluation of hematogenous ischemia is performed by various techniques and medical treatment is conducted according to the evaluation. In recent years, there is an increasing demand to evaluate an actual treatment effect before treatment is conducted.

BRIEF DESCRIPTION OF THE DRAWINGS

FIG. 1 is a diagram illustrating an example of a configuration of a medical information processing system according to a first embodiment.

FIG. 2 is a diagram illustrating an example of a configuration of a medical information processing apparatus according to the first embodiment.

FIG. 4 is a diagram for explaining a time phase used for fluid analysis according to the first embodiment.

FIG. 9 is a flowchart illustrating the flow of a process performed by the medical information processing apparatus according to the first embodiment.

FIG. 11A is a schematic gram illustrating an example of a change in a display orientation by a determination function according to the second embodiment.

FIG. 11B is a schematic diagram illustrating an example of a change in the display orientation by the determination function according to the second embodiment.

DETAILED DESCRIPTION

Figure 3:
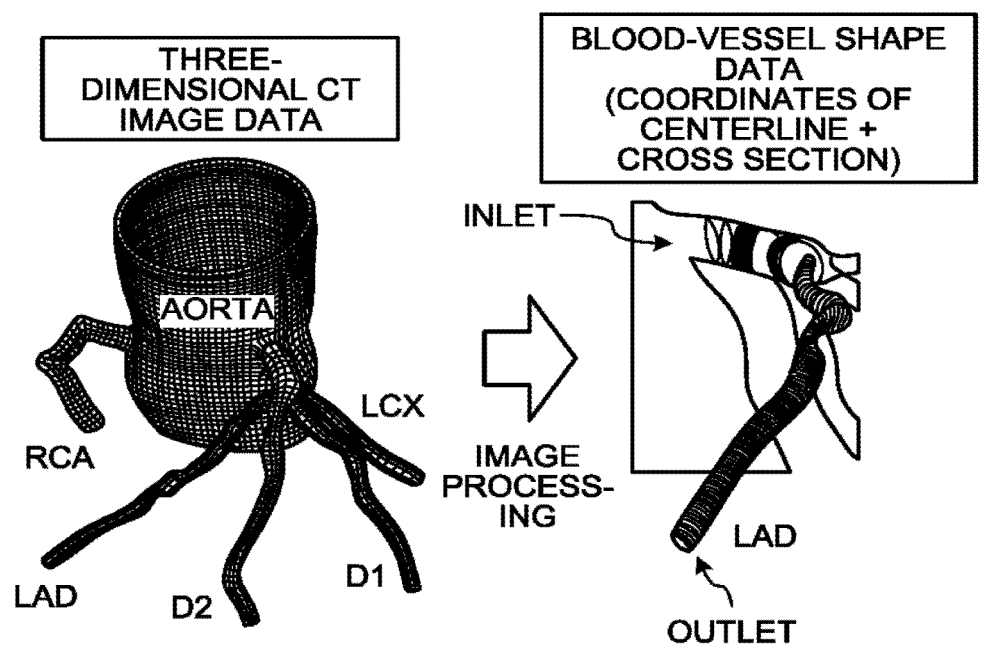
FIG. 3 is a diagram for explaining an example of a process by a control function according to the first embodiment.

According to an embodiment, a medical information processing apparatus includes processing circuitry. The processing circuitry is configured to acquire a first index value obtained based on fluid analysis that is performed based on an image including a blood vessel of a subject, the first index value being related to blood flow at each of positions in the blood vessel. The processing circuitry is configured to acquire external information including a second index value related to blood flow at each of the positions in the blood vessel. The processing circuitry is configured to change one of an arrangement direction of index values in a first graph and an arrangement direction of index values in a second graph in accordance with the other one of the arrangement directions, the first graph being a graph in which the first index value at each of positions in a long axis direction of the blood vessel is plotted, and the second graph being a graph in which the second index value at each of the positions in the long axis direction of the blood vessel is plotted. The processing circuitry is configured to display the first graph and the second graph on a display unit such that the arrangement directions of the index values match each other.

Embodiments of a medical information processing apparatus and a medical information processing method according to the present application will be described in detail below with reference to the accompanying drawings. The medical information processing apparatus and the medical information processing method according to the present application are not limited by the embodiments described below.

First Embodiment

A first embodiment will be described below. In the first embodiment, an example will be described in which a technique according to this application is applied to a medical information processing apparatus. Hereinafter, a medical information processing system including the medical information processing apparatus will be described as an example. Furthermore, as an example, a case will be described in which a blood vessel in a heart is used as an analysis target.

FIG. 1 is a diagram illustrating an example of a configuration of the medical information processing system according to the first embodiment. As illustrated in FIG. 1, the medical information processing system according to the first embodiment includes an X-ray computer tomography (CT) apparatus 100, an image storage apparatus 200, and a medical information procession apparatus 300.

For example, as illustrated in FIG. 1, the medical information processing apparatus 300 according to the first embodiment is connected to the X-ray CT apparatus 100 and the image storage apparatus 200 via a network 400. The medical information processing system may be further connected to a different medical image diagnostic apparatus, such as a magnetic resonance imaging (MRI) apparatus, an ultrasonic diagnostic apparatus, or a position emission tomography (PET) apparatus, via the network 400.

The X-ray CT apparatus 100 collects CT image data (volume data) on a subject. Specifically, the X-ray CT apparatus 100 causes an X-ray tube and an X-ray detector to rotate substantially around the subject to detect X-rays transmitted through the subject and collect projection data. The X-ray CT apparatus 100 generates time-series three-dimensional CT image data based on the collected projection data.

The image storage apparatus 200 stores therein image data collected by various medical image diagnostic apparatuses. For example, the image storage apparatus 200 is implemented by a computer apparatus, such as a server apparatus. In the first embodiment, the image storage apparatus 200 acquires CT image data (volume data) from the X-ray CT apparatus 100 via the network 400 and stores the acquired CT image data in a memory provided inside or outside the apparatus.

The medical information processing apparatus 300 acquires image data from various medical image diagnostic apparatuses via the network 400 and processes the acquired image data. For example, the medical information processing apparatus 300 is implemented by a computer apparatus, such as a workstation. In the first embodiment, the medical information processing apparatus 300 acquires CT image data from the X-ray CT apparatus 100 or the image storage apparatus 200 via the network 400, and performs various kinds of image processing on the acquired CT image data. The medical information processing apparatus 300 displays, on a display or the like, the CT image data that has not been subjected to the image processing or that has been subjected to the image processing. The medical information processing apparatus 300 may be installed in various locations. For example, the medical information processing apparatus 300 may be installed in a CT room in which the X-ray CT apparatus 100 is installed, a catheter operation room in which various operations using catheter are conducted, a radiologic interpretation room in which radiologic interpretation of images is conducted, or the like. When the medical information processing apparatuses 300 are installed in a plurality of locations, the medical information processing apparatus 300 is installed in each of the locations.

FIG. 2 is a diagram illustrating an example of a configuration of the medical information processing apparatus 300 according to the first embodiment. For example, as illustrated in FIG. 2, the medical information processing apparatus 300 includes an interface (I/F) circuitry 310, a memory 320, an input interface 330, a display 340, and processing circuitry 350.

The I/F circuitry 310 is connected to the processing circuitry 350, and controls transmission various kinds of data and communication performed with various medical image diagnostic apparatuses or the image storage apparatus 200 connected via the network 400. For example, the I/F circuitry 310 is implemented by a network card, a network adapter, a network interface controller (NIC), or the like. In the first embodiment, the T/F circuitry 310 receives CT image data from the X-ray CT apparatus 100 or the image storage apparatus 200, and outputs the received CT image data to the processing circuitry 350.

The memory 320 is connected to the processing circuitry 350 and stores therein various kinds of data. For example, the memory 320 is implemented by a semiconductor memory device, such as a random access memory (RAM) or a flash memory, a hard disk, an optical disk, or the like. In the first embodiment, the memory 320 stores therein CT image data received from the X-ray CT apparatus 100 or the image storage apparatus 200. Furthermore, the memory 320 stores therein a processing result obtained by the processing circuitry 350.

The input interface 330 is connected to the processing circuitry 350, converts an input operation received from an operator into an electric signal, and outputs the electric signal to the processing circuitry 350. For example, the input interface 330 is implemented by a trackball, a switch button, a mouse, a keyboard, a touch panel, or the like.

The display 340 is connected to the processing circuitry 350 and displays various kinds of information and various kinds of image data output from the processing circuitry 350. For example, the display 340 is implemented by a liquid crystal monitor, a cathode ray tube (CRT) monitor, a touch panel, or the like.

The processing circuitry 350 controls each of the components included in the medical information processing apparatus 300, in accordance with an input operation that is received from an operator via the input interface 330. For example, the processing circuitry 350 is implemented by a processor. In the first embodiment, the processing circuitry 350 stores CT image data output from the I/F circuitry 310 in the memory 320. Furthermore, the processing circuitry 350 reads CT image data from the memory 320 and displays the CT image data on the display 340.

With this configuration, the medical information processing apparatus 300 according to the first embodiment can improve the visibility of a graph of an index related to blood flow. Specifically, the medical information processing apparatus 300 determines a display orientation of the graph of the index related to blood flow based on external information, and displays the graph in the determined orientation to improve the visibility of the graph. The medical information processing apparatus 300 is able to perform a process of determining the display orientation in accordance with an environment in which the graph is to be displayed, and a process of determining the display orientation in accordance with other graphs to be displayed for comparison. The processes are sequentially described below.

To perform the processes as described above, as illustrated in FIG. 2, the processing circuitry 350 in the medical information processing apparatus 300 according to the first embodiment executes a control function 351, a generation function 352, a determination function 353, and a display control function 354. The processing circuitry 350 is one example of processing circuitry in the appended claims.

The control function 351 controls the entire medical information processing apparatus 300. For example, the control function 351 controls various processes corresponding to electric signals received from the input interface 330. As one example, the control function 351 controls acquisition of CT image data via the I/F circuitry 310, storage of the acquired CT image data in the memory 320, or the like. Furthermore, for example, the control function 351 controls read of CT image data stored in the memory 320 and generation of a display image from the read CT image data. As one example, the control function 351 performs various kinds of image processing on CT image data to generate an image of a blood vessel. For example, the control function 351 performs image processing on CT image data to generate a volume rendering image, a curved multi planer reconstruction (CPR) image, a multi planer reconstruction (MPR) image, a stretched multi planer reconstruction (SPR) image, or the like. Furthermore, the control function 351 acquires an index value related to blood flow at each of positions in a blood vessel, where the index value is obtained based on fluid analysis that is performed based on an image including the blood vessel of a subject. The control function 351 is able to acquire the index value by performing the fluid analysis, and is also able to acquire a result of the fluid analysis via the network 400. Hereinafter, a case will be described in which the control function 351 performs the fluid analysis.

The control function 351 performs fluid analysis based on CT image data. Specifically, the control function 351 performs fluid analysis based on an image including a blood vessel of a subject, and obtains an index value related to blood flow at each of positions in the blood vessel. More specifically, the control function 351 extracts time-series blood-vessel shape data, which indicates the shape of a blood vessel, from three-dimensional CT image data. For example, the control function 351 reads CT image data in a plurality of time phases, which is collected over time, from the memory 320, and performs image processing on the read CT image data in the plurality of time phases to extract the time-series blood-vessel shape data.

Here, the control function 351 sets a target region, for which an index value related to blood flow is to be calculated, in a blood vessel region included in CT image data. Specifically, the control function 351 sets the target region in the blood vessel region in accordance with an instruction or image processing performed by an operator via the input interface 330. Then, the control function 351 extracts, as the blood-vessel shape data of the set target region, the centerline of the blood vessel (coordinate information on the centerline), cross-sectional areas of blood vessel and a lumen in a cross section perpendicular to the centerline, a distance from the centerline to an inner wall and a distance from the centerline to an outer wall in a cylinder direction in the cross section perpendicular to the centerline, or the like from the CT image data. The control function 351 may extract various other kinds of blood-vessel shape data depending on analysis techniques.

Furthermore, the control function 351 sets an analysis condition of the fluid analysis. Specifically, the control function 351 sets, as the analysis condition, a physical property value of blood, a condition of iterative calculation, a default value of analysis, or the like. For example, the control function 351 sets, as the physical property value of blood, a viscosity of blood, a density of blood, or the like. Furthermore, the control function 351 sets, as the condition of iterative calculation, the maximum number of times of iteration in the iterative calculation, a relaxation coefficient, an allowable value of a residual error, or the like. Moreover, the control function 351 sets, as the default value of analysis, a default value of a flow rate, a pressure, a fluid resistance, a pressure boundary, or the like. Various values used by the control function 351 may be incorporated in the system in advance, or may be defined interactively by an operator.

The control function 351 calculates an index related to blood flow of a blood vessel through fluid analysis using image data including the blood vessel (for example, a coronary artery or the like). Specifically, the control function 351 performs fluid analysis using the blood-vessel shape data and the analysis condition, and calculates the index related to the blood flow in the target region of the blood vessel. For example, the control function 351 calculates an index, such as a pressure, a blood flow rate, a blood flow velocity, a vector, or a shear stress, at each of predetermined positions in the blood vessel, based on the blood-vessel shape data, such as the contour of the lumen, the outer wall of the blood vessel, the cross-sectional area of the blood vessel, or the centerline of the blood vessel, and based on the set condition, such as the physical property value of blood, the condition of iterative calculation, or the default value of analysis. The control function 351 also calculates a temporal change in the index, such as the pressure, the blood flow rate, the blood flow velocity, the vector, or the shear stress, by using a temporal change in the blood-vessel shape data, such as the contour of the lumen or the outer wall of the blood vessel, the cross-sectional area of the blood vessel, or the centerline of the blood vessel.

FIG. 3 is a diagram for explaining an example of a process by the control function 351 according to the first embodiment. As illustrated in FIG. 3, for example, the control function 351 extracts blood-vessel shape data including the coordinates of the centerline and information on a cross section with respect to a left anterior descending artery (LAD) as a target region, from three-dimensional CT image data including an aorta and a coronary artery. Furthermore, the control function 351 sets an analysis condition for analysis for the extracted LAD as the target. Then, the control function 351 performs fluid analysis using the extracted blood-vessel shape data on the LAD and the set condition to calculate the index, such as the pressure, the blood flow rate, the blood flow velocity, the vector, or the shear stress, at each of predetermined positions along the centerline from inlet boundary to the outlet boundary of the target region LAD, for example. That is, the control function 351 calculates a distribution of the pressure, the blood flow rate, the blood flow velocity, the vector, the shear stress, or the like for the target region.

As described above, the control function 351 extracts pieces of blood-vessel shape data from each of the pieces of the CT image data in the plurality of time phases collected over time, and performs fluid analysis using the pieces of the extracted blood-vessel shape data in the plurality of time phases and the analysis condition to calculate the index related to the blood flow. Here, the control function 351 calculates an analysis result with higher accuracy by using CT image data in a plurality of time phases in which the cardiac phase falls within a predetermined range.

FIG. 4 is a diagram for explaining the time phase used for the fluid analysis according to the first embodiment. In FIG. 4, the upper section indicates a heart rate, the middle section indicates movement of the heart, and the lower section indicates the area of the coronary artery. Furthermore, in FIG. 4, the horizontal direction indicates time, and, temporal changes in the heart rate, the movement of the heart, and the area of the coronary artery are illustrated in an associated manner. For example, the control function 351 performs fluid analysis by using CT image data in cardiac phases included in the range of cardiac phases of 70% to 99%. As illustrated in FIG. 4, the cardiac phases of 70% to 99% are time phases in which the heart does not move much and the area of the coronary artery changes largely. The heart moves with contraction and expansion, and the movement of the heart is stable in the latter half of a diastole (in the cardiac phases of 70% to 99%) as illustrated in the middle section of FIG. 4. That is, the control function 351 can use CT image data including little movements with the heartbeat, by using the CT image data in the cardiac phase included in the cardiac phases of 70% to 99% in which the movement of the heart is stable.

Furthermore, as illustrated in the lower section of FIG. 4, the area of the coronary artery becomes the largest in the cardiac phase of around 70% and becomes the smallest in the cardiac phase of around 99%. This is because blood starts to flow into the coronary artery in the cardiac phase of around 70% and then flows out as the cardiac phase approaches 99%. The control function 351 calculates an analysis result with higher accuracy by using the CT image data in the plurality of time phases in the range of the cardiac phases of 70% to 99% such that a change in the area of the coronary artery can be included as much as possible.

Furthermore, the control function 351 calculates a myocardial fractional flow reserve (FFR) based on a distribution of a pressure in the target region. Specifically, the control function 351 calculates an FFR, which is an index to estimate how much blood flow is inhibited by a lesion, based on pressures on the upstream side and the downstream side of a predetermined position in a blood vessel (for example, a lesion site, such as a stenosis or a plague). The control function 351 according to the present application is able to calculate various pressure indexes as the FFR.

The definition of the FFR is described below. As described above, the FFR is an index for estimating how much blood flow is inhibited by a lesion (for example, a stenosis or a plague). The FFR is defined by a ratio of a flow rate that is obtained when there is no lesion to a flow rate that is obtained when there is a lesion, and is calculated by Expression (1) below. In Expression (1), "Qn" denotes the flow rate that is obtained when there is no lesion, and "Qs" denotes the flow rate that is obtained when there is a lesion.

$$FFR \equiv \frac{Qs}{Qn} \tag{1}$$

As indicated by Expression (1), for example, the FFR is defined by the equation of division of "Qs" by "Qn". In general, to calculate the FFR, adenosine is administered to a subject to obtain the maximum hyperemia state (stressed state), so that the relationship between the flow rate and the pressure in a blood vessel can be represented as a proportional relationship and the FFR can be replaced with the definition of a pressure. That is, by representing the relationship between the flow rate and the pressure in the blood vessel as a proportional relationship, Expression (1) can be represented as Expression (2) below. In Expression (2), "Pa" denotes a pressure on the upstream side of a lesion, and "Pd" denotes a pressure on the downstream side of the lesion. Furthermore, "Pv" denotes a pressure of the right atrium to which venous blood flows from all over the body.

$$FFR \equiv \frac{Qs}{Qn} = \frac{Pd - Pv}{Pa - Pv} \tag{2}$$

For example, by representing the relationship between the flow rate and the pressure in a blood vessel as a proportional relationship, "Qs" may be represented as "Pd–Pv" and "Qn" may be represented as "Pa–Pv" as indicated in Expression (2). That is, the FFR is represented by a ratio between values that are obtained by subtracting the pressure at the base line of the blood vessel from the pressure on the upstream side of the lesion and from the pressure on the downstream side of the lesion.

In the stressed state in which adenosine is administered to the subject, it is possible to handle the values such that "Pa>>Pv" and "Pd>>Pv"; therefore, Expression may be regarded as Expression (3) below.

$$FFR \equiv \frac{Qs}{Qn} = \frac{Pd - Pv}{Pa - Pv} \approx \frac{Pd}{Pa} \tag{3}$$

Specifically, as illustrated in Expression (3), the FFR is calculated by the equation of division of "Pd" by "Pa". For example, the control function 351 assigns the calculated pressure on the upstream side of the lesion and the calculated pressure on the downstream side of the lesion to the above-described Expression (3) to calculate the value of the FFR at each of positions in the blood vessel.

In the above-described calculation of the FFR, a case has been described in which adenosine is administered to a subject to obtain a stressed state so that the relationship between the flow rate and the pressure in a blood vessel can be represented as a proportional relationship and the FFR can be replaced with the definition of a pressure. However, in the calculation of the FFR, it may be possible to employ a subject in a resting state and perform the calculation by replacing the FFR with the definition of a pressure. In this case, even in the resting state in which adenosine is not administered, the relationship between the flow rate and the pressure in a blood vessel is represented as a proportional relationship during a wave-free period in the cardiac cycle (a period in which vascular resistance is small and stable); therefore, the FFR is calculated by using a pressure during the wave-free period in the resting state (hereinafter, the FFR calculated during the wave-free period in the resting state may be described as an instantaneous FFR).

The instantaneous FFR is an index that contributes to reduce load on a subject because adenosine is not administered and that has characteristics (for example, it can reflect the effect of the heart muscle or it can be measured even if a plurality of stenoses are observed in a single blood vessel) which are not observed in the FFR; therefore, the instantaneous FFR is attracting attention in recent years. In the calculation of the FFR using image data, CT image data in the cardiac phases of 70% to 99% as described above is used as CT image data in the wave-free period. Specifically, the relationship between the flow rate and the pressure in a blood vessel is represented as a proportional relationship in the cardiac phases of 70% to and therefore, if CT image data in these cardiac phases used, it is possible to calculate the FFR based on the pressure by the above-described Expression (3) even when the CT image data is collected from a subject in the resting state.

Furthermore, if a pressure "P0" at zero flow rate, which is the pressure in a blood vessel when the flow rate in the blood vessel is "0", is used as a base line to be subtracted from the pressure on the upstream side of the lesion and the pressure on the downstream side of the lesion, the control function 351 can more accurately express a proportional relationship between the flow rate and the pressure as compared to the case where the pressure "Pv" of the right atrium is used as the base line. In this case, the control function 351 assigns the pressure on the upstream side of the lesion site, the pressure on the downstream side of the lesion site, and the pressure at zero flow rate to Expression (4) below to calculate the value of the FFR at each of the positions in the blood vessel. In Expression (4), "Pa" denotes the pressure on the upstream side of the lesion (for example, a stenosis), and "Pd" denotes the pressure on the downstream side of the lesion (for example, a stenosis). Furthermore, in Expression (4), "P0" denotes the pressure at zero flow rate. The pressure at zero flow rate is estimated by searching for a pressure at which the flow rate and the flow velocity become zero in the fluid analysis performed by the control function 351.

$$FFR \equiv \frac{Qs}{Qn} = \frac{Pd - P0}{Pa - P0} \quad (4)$$

Here, the pressure "P0" at zero flow rate indicates a higher value than "Pv" in both of the stressed state and the resting state. This is because there is vascular resistance, and even in the state such as "P0>Pv", blood does not flow and the flow rate becomes zero. Furthermore, "P0" during the wave-free period in the resting state indicates a higher value than "P0" in the stressed state. This is because there is a difference in myocardial resistance between the stressed state and the resting state. For example, when a blood vessel expands in the stressed state, the resistance decreases, so that the value of "P0" at the time the blood flow is zero becomes closer to the value of "Pv" as compared to the resting state. In contrast, in the case of the resting state, the resistance is larger than the resistance in the stressed state; therefore, the value of "P0" at the time the blood flow is zero becomes larger than the value of "Pv". Therefore, for example, when CT image data during the wave-free period in the resting state is used, the control function 351 calculates the FFR based on the expression in which "P0" is taken into account as indicated by Expression (4).

When CT image data during the wave-free period in the resting state is used, the control function 351 may calculate the FFR by using the above-described Expression (2). In this case, the control function 351 assigns the pressure on the upstream side of the lesion site, the pressure on the downstream side of the lesion site, and "Pv" to Expression (2) to calculate the value of the FFR at each position in the blood vessel. Hereinafter, the above-described pressure indexes are collectively referred to as the FFR.

Figure 5A:
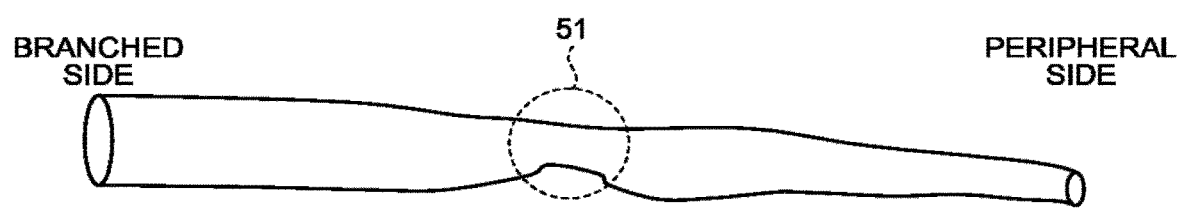
FIG. 5A is a diagram for explaining generation of a graph by a generation function according to the first embodiment.
Figure 5B:
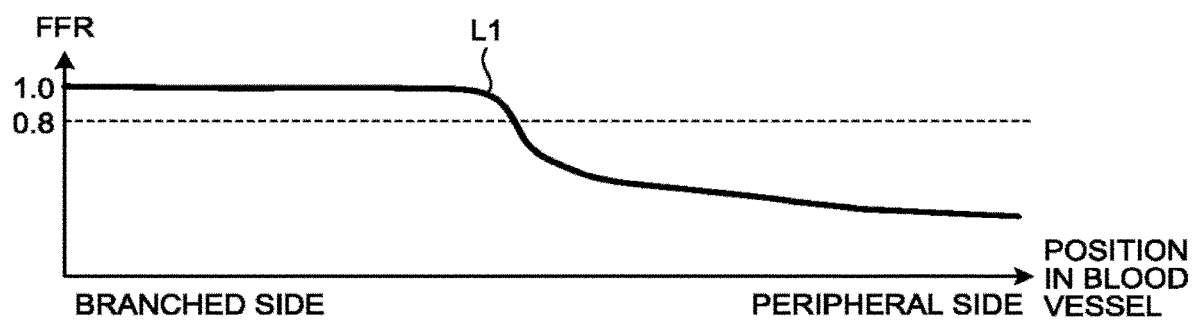
FIG. 5B is a diagram for explaining generation of a graph by the generation function according to the first embodiment.

Referring back to FIG. 2, the generation function 352 generates a graph by using the index values related to the blood flow, which are calculated by the control function 351. Specifically, the generation function 352 generates a graph indicating the index value at each of positions in the blood vessel. For example, the generation function 352 generates a graph indicating the value of the FFR at each of positions in the blood vessel. FIG. 5A and FIG. 5B are diagrams for explaining generation of a graph by the generation function 352 according to the first embodiment. FIG. 5A illustrates an example of a blood vessel on which the fluid analysis has been performed by the control function 351. FIG. 5B illustrates an example of the graph generated by the generation function 352.

For example, the generation function 552 acquires the values of the FFR at positions from a position or the branched side to a position on the peripheral side subjected to the fluid analysis in the blood vessel illustrated in FIG. 5A, and generates a graph as illustrated in FIG. 5B by using the acquired values of the FFR. As one example, as illustrated in FIG. 5B, the generation function 352 generates a graph in which the horizontal axis represents the positions in the blood vessel and the vertical axis represents the values of the FFR. In this case, the generation function 352 may generate a graph in which an auxiliary line for evaluating the values of the FFR is added. For example, the generation function 352 generates a graph in which an auxiliary line is added at the position of "0.8" as illustrated in FIG. 5B.

In the graph of the FFR generated by the generation function 352, the value gradually decreases from the branched side to the peripheral side; however, if a stenosis 51 has occurred in the blood vessel as illustrated in FIG. 5A for example, the value of the FFR largely decreases at a corresponding position in the graph as indicated by a curved line L1. A medical doctor makes a diagnosis on whether to conduct percutaneous coronary intervention (PCI) or whether to perform drug treatment, for example.

When displaying the graph as described above, the medical information processing apparatus 300 according to the first embodiment determines a display orientation based on external information in order to improve the visibility of the graph. As described above, a method using a pressure wire is mainly used in the current FFR measurement, and a similar graph is displayed in this method. However, in the method using a pressure wire, it is often the case that the display orientation of the graph is opposite to the orientation of the graph illustrated in FIG. 5B due to the characteristics of the measurement method.

Figure 6:
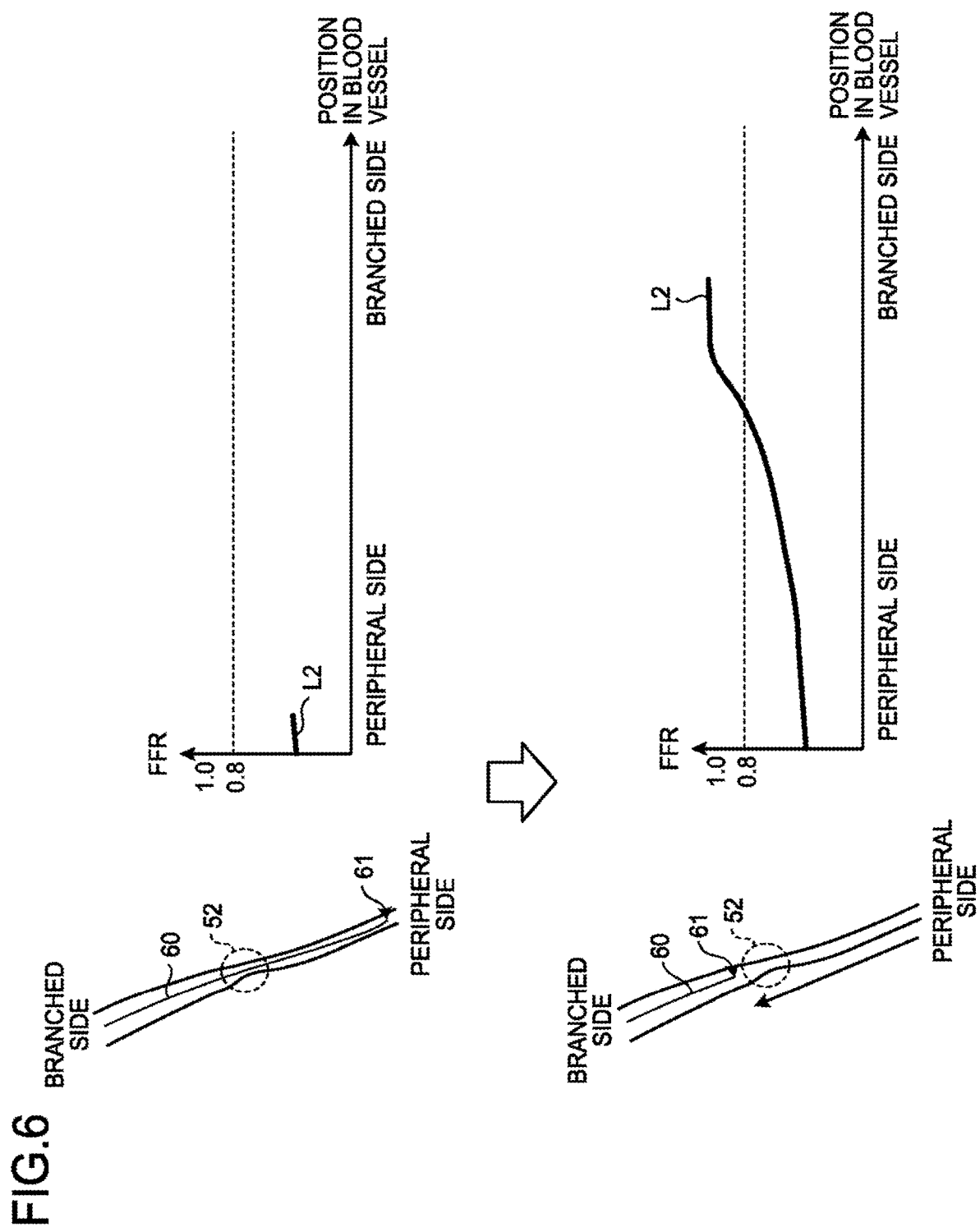
FIG. 6 is a diagram illustrating an example of a graph displayed by an FFR measurement apparatus in FFR measurement using a pressure wire.

FIG. 6 is a diagram illustrating an example of a graph displayed on an FFR measurement apparatus in FFR measurement using a pressure wire. For example, in the FFR measurement using a pressure wire, as illustrated in the upper section of FIG. 6, a pressure wire 60 is first inserted until the peripheral side of a target region of a blood vessel and then pulled back while a sensor 61 measures a pressure at each of positions, so that the values of the FFR are calculated. In this manner, in the method using a pressure wire, values are displayed in real time based on results acquired while the pressure wire is pulled back; therefore, the display orientation of the graph is opposite to the orientation illustrated in FIG. 5B.

That is, in real-time display using a pressure wire, as indicated by a curved line L2 in FIG. 6, the values of the pressure are acquired from the peripheral side and the graph is gradually generated based on the acquired values; therefore, the left side of the graph represents the peripheral side and the right side of the graph represents the branched side. In this case, as illustrated in the lower section of FIG. 6, the graph is generated such that the value of the FFR gradually increases from the peripheral side to the branched side and the value of the FFR largely increases when the sensor 61 passes through a stenosis 52.

In contrast, when the FFR is calculated by fluid analysis, a graph is generated after the values of the FFR at the respective positions in the blood vessel are calculated; therefore, it is often the case that a graph in which the left side represents the branched side and the right side represents the peripheral side as illustrated in FIG. 5B is generated. In this manner, when the FFR is calculated by fluid analysis, the display orientation of the graph may be opposite as compared to the case where the FFR is measured by using a pressure wire. Therefore, when an operator who is familiar with a graph using a pressure wire refers to a graph in the display orientation as illustrated in FIG. 5B, the visibility may be reduced.

Therefore, the medical information processing apparatus 300 according to the first embodiment determines a display orientation of a graph based on a location in which the graph is used, an operator, or various kinds of external information, and displays the graph in the determined display orientation to provide a familiar graph at any time and improve the visibility of the graph.

Referring back to FIG. 2, the determination function 35 determines, in a graph of an index value related to blood flow at each of positions in the long axis direction of a blood vessel, an arrangement direction of the index values based on external information. Specifically, the determination function 353 is connected to an external apparatus, and acquires external information, which indicates an environment in which the index value is observed, from the external apparatus. That is, the determination function 353 acquires the external information from the external apparatus, and determines the environment in which the index values are observed based on the external information. Then, in a graph in which the index values that are related to the blood flow at the respective positions in the long axis direction of the blood vessel and that are obtained by the control function 351 are plotted, the determination function 353 determines the arrangement direction of the index values based on the external information. That is, the determination function 353 determines the arrangement direction of the index values based on the determined environment. For example, the determination function 353 determines the arrangement direction of the index values in the graph based on information on a location in which the graph is displayed (a location in which the display 340 is installed), information on an operator, image information, a reception signal from the external apparatus, or information on a subject.

For example, in the case of a graph in which the vertical axis represents the index values and the horizontal axis represents the positions in the long axis direction of the blood vessel, the determination function 353 determines on which one of the left side and the right side of the graph the index value on the peripheral side of the blood vessel is to be arranged, based on the external information. In other words, the determination function 353 determines the environment in which the index values are observed based on the external information, and determines on which one of the left side and the right side of the graph the index value on the branched side of the blood vessel is to be arranged.

The external information will be described below. As described above, the external information may be the information on a location in which the graph is displayed (a location in which the display 340 is installed), the information on an operator, the image information, information including the reception signal from the external apparatus, the information on the subject, or the like. Examples of the location in which the graph is displayed (the location in which the display 340 is installed) include a CT room, a catheter operation room, and a radiologic interpretation room. Furthermore, the information on an operator is, for example, information on an operator who operates the medical information processing apparatus 300, and is information for specifying a graph that is usually referred to. Moreover, examples of the image information include information indicating a type of an image to be displayed together with the graph. Furthermore, examples of the reception signal from the external apparatus include a signal received from a medical image diagnostic apparatus, such as an FFR measurement apparatus that performs FFR measurement using a pressure wire, an X-ray CT apparatus, or an angiography apparatus. Moreover, examples of the information on a subject include information on a medical record. The determination function 353 determines the environment in which the index values are observed based on the external information as described above, and determines the display orientation in accordance with the determination result.

For example, if the information on a location is used, the information on a location is stored in the memory 320 in advance when the medical information processing apparatus 300 is installed, or the information on a location is input when an operator is authenticated, and the determination function 353 determines the display orientation by using the provided information. That is, the determination function 353 reads the information on a location stored in the memory 320 and determines the arrangement direction of the index values in the graph based on the read information. Alternatively, the determination function 353 determines the arrangement direction of the index values in the graph based on the information on a location that is input when an operator is authenticated.

Figure 7A:
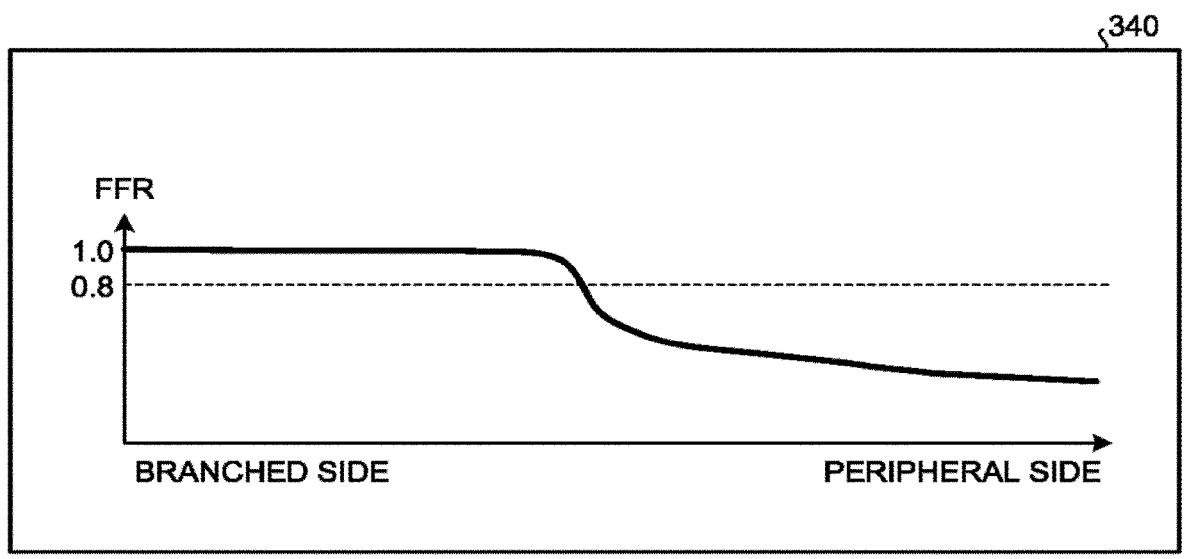
FIG. 7A is a diagram for explaining an example of determination of an arrangement direction of index values by a determination function according to the first embodiment.
Figure 7B:
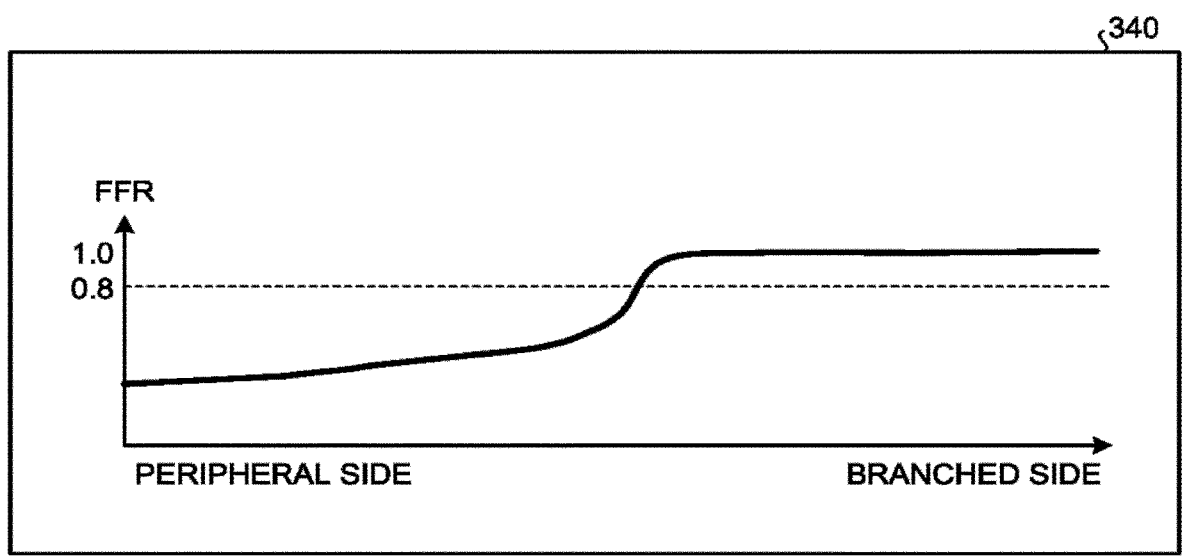
FIG. 7B is a diagram for explaining an example of determination of the arrangement direction of the index values by the determination function according to the first embodiment.

FIG. 7A and FIG. 7B are diagrams for explaining determination of the arrangement direction of the index values by the determination function 353 according to the first embodiment. For example, when the information on a location in which the graph is displayed indicates a CT room or a radiologic interpretation room, the determination function 353 makes a determination to display the graph such that the branched side is arranged on the left side as illustrated in FIG. 7A. In contrast, for example, when the information on a location in which the graph is displayed indicates a catheter operation room, the determination function 353 makes a determination to display the graph such that the peripheral side is arranged on the left side as illustrated in FIG. 7B. That is, in the case of the catheter operation room in which a graph is usually displayed by the FFR measurement apparatus, the determination function 353 determines the display orientation to display a graph such that the peripheral side is arranged on the left side, similarly to a graph that is displayed by the FFR measurement apparatus. In contrast, in the case of the CT room or the radiologic interpretation room in which a graph is rarely displayed by the FFR measurement apparatus, the determination function 353 determines the display orientation to display a graph such that the branched side is arranged on the left side, similarly to a graph that is displayed when the FFR is calculated through fluid analysis.

In this manner, the determination function 355 determines the display orientation of a graph such that the graph is displayed in accordance with the display orientation of a graph that is usually referred to. That is, the determination function 353 determines the display orientation of a graph based on the tendency of a graph to be referred to. The same applies when other kinds of information are used.

Furthermore, for example, when the information on an operator is used, the determination function 353 makes a determination to display a graph in which the branched side is arranged on the left side as illustrated in FIG. 7A for an operator who rarely refers to a graph displayed by the FFR measurement apparatus (who usually refers to a graph based on the FFR calculated through fluid analysis). In contrast, the determination function 353 makes a determination to display a graph in which the peripheral side is arranged on the left side as illustrated in FIG. 7B for an operator who usually refers to a graph displayed by an FFR measurement apparatus (who rarely refers to a graph based on the FFR calculated through fluid analysis).

Here, the operator may be identified based on operator information that is input at the time of authentication, for example. In this case, for example, the determination function identifies the operator based on information on professional affiliation, a role, or the like of the operator, which is input at the time of authentication. Furthermore, for example, it may be possible to store information in which the display orientation is set for a specific individual in the memory 320 in advance, and cause the determination function 353 to determine the display orientation by reading the display orientation set in advance from information on the operator input at the time of authentication.

Alternatively it may be possible to install a camera in each room, and identify the operator from image information on the operator captured by the camera. In this case, for example, the determination function 353 acquires an image captured by the camera and performs image processing on the acquired image to identify the operator. As one example, the determination function 353 performs processing, such as pattern matching, on the image and determines whether the captured operator wears scrub suits or gloves. When the operator wears scrub suits or gloves, the determination function 353 determines that the operator performs a catheter operation and determines that the operator usually refers to a graph displayed by the FFR measurement apparatus. In contrast, when the operator does not wear scrub suits or gloves, the determination function 353 determines that the operator does not perform an operation and determines that the operator rarely refers to a graph displayed by the FFR measurement apparatus.

Furthermore, for example, when the image information is used, the determination function 353 acquires image information to be referred to and determines whether the acquired image has high real-time property. For example, if an image to be referred to is a past image and acquired from the image storage apparatus 200, the determination function 353 determines that the real-time property of the image is low. In contrast, for example, when the acquisition time of an image to be referred to corresponds to a current time and the image is a moving image directly acquired from an angiography apparatus, the determination function 353 determines that the real-time property of the image is high.

Then, in the case of the image with low real-time property, the determination function 353 makes a determination to display a graph in which the branched side is arranged on the left side as illustrated in FIG. 7A. In contrast, in the case of the image with high real-time property, the determination function 353 makes a determination to display a graph in which the peripheral side is arranged on the left side as illustrated in FIG. 7B.

Furthermore, for example, when the reception signal from the external apparatus is used, the determination function 353 receives a signal from the external apparatus and determines, based on the received signal, a situation in which a graph is to be referred to. That is, the determination function 353 determines whether a graph displayed by the FFR measurement apparatus is likely to be referred to in the situation, based on the signal received from the external apparatus. As one example, when receiving a signal from the FFR measurement apparatus, the determination function 353 determines that a graph displayed by the FFR measurement apparatus is likely to be referred to in the situation, and makes a determination to display the graph such that the peripheral side is arranged on the left side as illustrated in FIG. 7B. Furthermore, when receiving a signal related to real-time processing from an angiography apparatus (for example, a signal indicating that fluoroscopy is conducted), the determination function 353 determines that a graph displayed by the FFR measurement apparatus is likely to be referred to in the situation, and makes a determination to display the graph such that the peripheral side is arranged on the left side as illustrated in FIG. 7B.

Moreover, for example, when the information on a medical record is used, determination function 353 reads a past display orientation from a medical record, and determines a display orientation such that the display orientation becomes the same as the read display orientation. That is, the orientation of the graph displayed in the past is input in the medical record, and when fluid analysis is performed on the same subject again, the determination function 353 determines the arrangement direction such that the index values are arranged in the same direction as the orientation of the graph recorded in the medical record.

As described above, the determination function 353 determines a situation in which the graph is to be displayed by using various kinds of external information, and determines the display orientation of the graph in accordance with the determined situation.

Figure 8A:
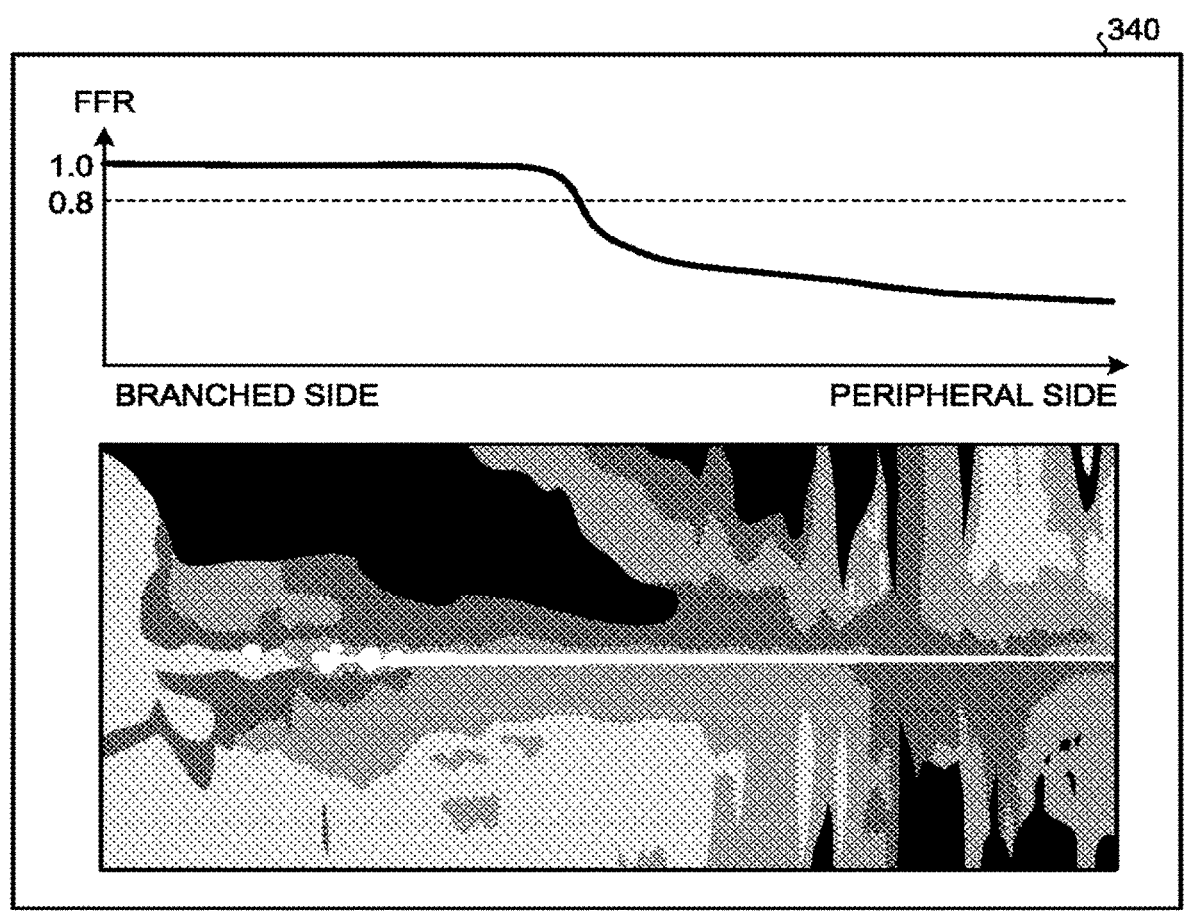
FIG. 8A is a diagram for explaining an example of display information displayed by a display control function according to the first embodiment.
Figure 8B:
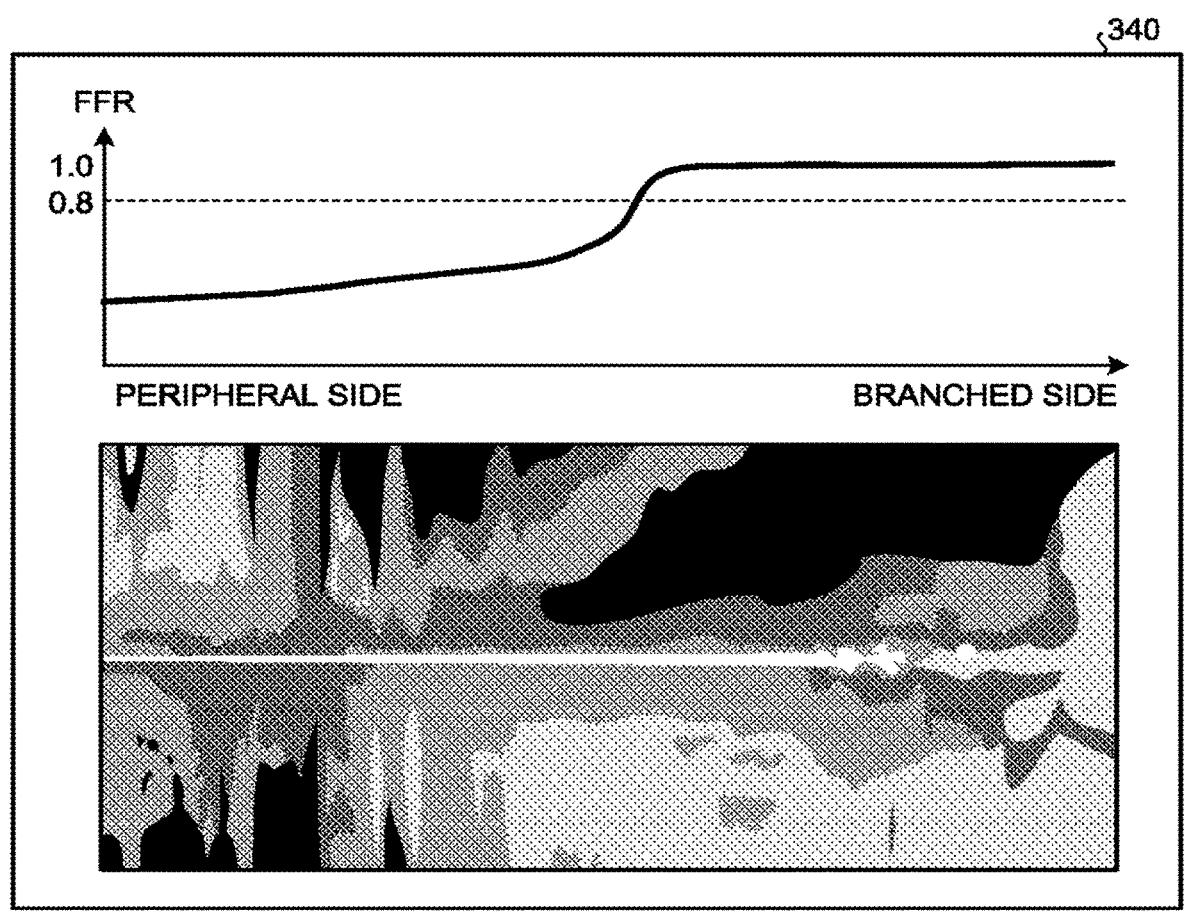
FIG. 8B is a diagram for explaining an example of the display information displayed by the display control function according to the first embodiment.

Referring back to FIG. 2, the display control function 354 displays a graph, in which the index values are arranged in the arrangement direction determined by the determination function 353, on the display 340. For example, when the determination function 353 determines whether the display 340 is located in an operating room by using the above-described various kinds of information, the display control function 354 displays the peripheral side on the left side when the determination function 353 determines that the display 340 is located in the operating room, whereas the display control function 354 displays the peripheral side on the right side when the determination function 353 determines that the display 340 is located in other places. FIG. 8A and FIG. 8B illustrate examples of display information displayed by the display control function 354 according to the first embodiment. For example, the display control function 354 displays a graph in which the branched side is arranged on the left side as illustrated in FIG. 8A, in accordance with the determination performed by the determination function 353. Furthermore, for example, the display control function 354 displays a graph in which the peripheral side is arranged on the left side as illustrated in FIG. 8B, in accordance with the determination performed by the determination function 353.

The display control function 354 is able to display an image together with a graph. Specifically, the display control function 354 further displays a medical image indicating the arrangement direction of the index values. For example, when displaying a graph in which the branched side is arranged on the left side, the display control function 354 displays an SPR image in which the branched side is arranged on the left side as illustrated in FIG. 9A. In contrast, when displaying a graph in which the peripheral side is arranged on the left side, the display control function 354 displays an SPR image in which the peripheral side is arranged on the left side as illustrated in FIG. The image to be displayed is not limited to the SPR image, but may be a volume rendering image or a CPR image.

Next, the flow of a process performed by the medical information processing apparatus 300 according to the first embodiment will be described. FIG. 9 is a flowchart illustrating the flow of a process performed by the medical information processing apparatus 300 according to the first embodiment. Step S101 and Step S102 in FIG. 9 are realized by, for example, causing the processing circuitry 350 to call a program corresponding to the control function 351 from the memory 320 and execute the program. Furthermore, Step S103 is realized by, for example, causing the processing circuitry 350 to call a program corresponding to the generation function 352 from the memory 320 and execute the program. Moreover, Step S104 and Step S105 are realized by, for example, causing the processing circuitry 350 to call a program corresponding to the determination function 353 from the memory 320 and execute the program. Furthermore, Step S106 is realized by, for example, causing the processing circuitry 350 to call a program corresponding to the display control function 354 from the memory 320 and execute the program.

In the medical information processing apparatus 300 according to the first embodiment, the processing circuitry 350 first performs fluid analysis using collected CT image data (Step S101), and calculates index values (for example, the FFR) related to blood flow (Step S102). Then, the processing circuitry 350 generates a graph (Step S103).

Subsequently, the processing circuitry 350 acquires external information (Step S104), and determines a display orientation of the graph based on the external information (Step S105). Thereafter, the processing circuitry 350 displays the graph in the determined orientation (Step S106).

As described above, according to the first embodiment, the determination function 353 determines, based on the external information, the arrangement direction of the values of the FFR in a graph indicating the values of the FFR at the respective positions in the long axis direction of the blood vessel. The display control function 354 displays, on the display 340, the graph in which the values of the FFR are arranged in the arrangement direction determined by the determination function 353. Therefore, the medical information processing apparatus 300 according to the first embodiment can display a graph that is usually referred to, and therefore can improve the visibility of the graph.

Furthermore, according to the first embodiment, the vertical axis of the graph represents the values of the FFR and the horizontal axis represents the positions in the long axis direction of a blood vessel. The determination function 353 determines on which one of the left side and the right side of the graph the value of the FFR on the peripheral side of the blood vessel is to be arranged, based on the external information. Therefore, the medical information processing apparatus 300 according to the first embodiment can improve the visibility of the graph that is mainly used at the moment.

Moreover, according to the first embodiment, the determination function 353 determines the arrangement direction of the values of the FFR based on the information on a location in which the graph is displayed, the information on an operator, the image information, the reception signal from the external apparatus, or the information on the subject. Therefore, the medical information processing apparatus 300 according to the first embodiment can determine the display orientation of the graph based on various situations, and therefore can display an appropriate graph in the various situations.

Furthermore, the display control function 354 according to the first embodiment further displays a medical image indicating the arrangement direction of the values of the FFR. Therefore, the medical information processing apparatus 300 according to the first embodiment can visually indicate the display orientation of the graph, and therefore can further improve the visibility.

Second Embodiment

While the first embodiment has been described above, various different embodiments other than the above-described first embodiment is applicable.

In the above-described first embodiment, a case has been described in which a graph in a landscape orientation is displayed. However, the embodiment is not limited to this example, and a graph may be displayed in arbitrary orientations. For example, the generation function 352 can generate a graph in which the horizontal axis represents the values of the FFR and the vertical axis represents the positions in the long axis direction of a blood vessel. In this case, the determination function determines the display orientation accordingly.

Figure 10A:
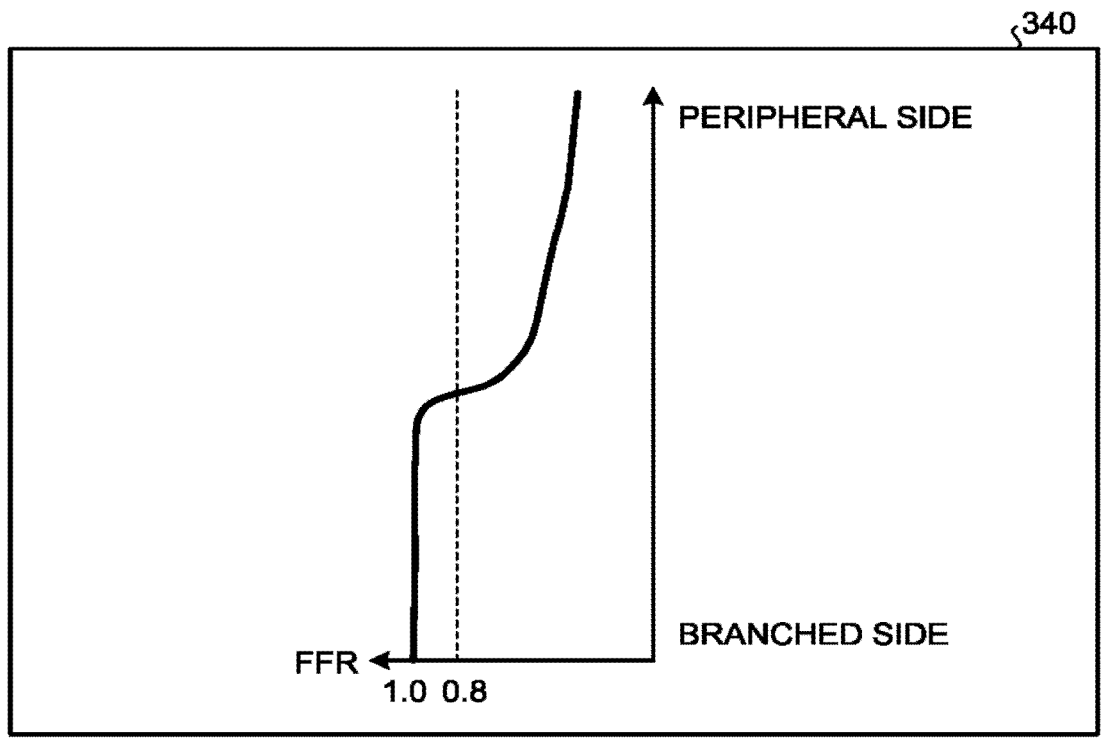
FIG. 10A is a diagram for explaining an example of determination of an arrangement direction of index values by a determination function according to a second embodiment.
Figure 10B:
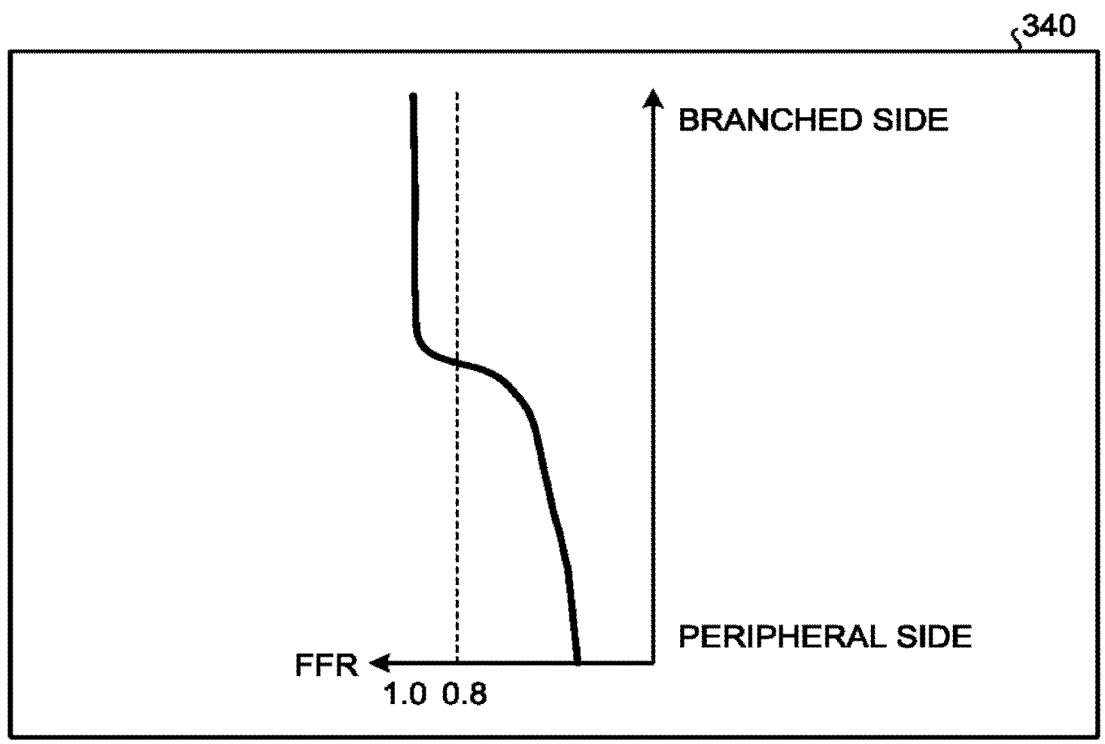
FIG. 10B is a diagram for explaining an example of determination of the arrangement direction of the index values by the determination function according to the second embodiment.

For example, the determination function 353 according to a second embodiment determines on which one of the upper side and the lower side of a graph the value of the FFR on the peripheral side of a blood vessel is to be arranged, based on external information. FIG. 10A and FIG. 10B are diagrams for explaining examples of determination of the arrangement direction of the index values by the determination function 353 according to the second embodiment. For example, in a situation similar to the situation in which the graph illustrated in FIG. 7A is obtained (in the situation in which a graph generated from the values of the FFR calculated through fluid analysis is likely to be referred to), the determination function 353 makes a determination to display a graph in which the branched side is arranged on the lower side as illustrated in FIG. 10A.

In contrast, in a situation similar to the situation in which the graph illustrated in FIG. 7B is obtained (in the situation in which a graph generated from the values of the FFR measured by the FFR measurement apparatus is likely to be referred to), the determination function 353 makes a determination to display a graph in which the peripheral side is arranged on the lower side as illustrated in FIG. 10B.

In the above-described first embodiment, a case has been described in which the FFR is displayed as the index related to blood flow. However, the embodiment is not limited to this example, and other indexes, such as a flow rate, a flow velocity, or a pressure, may be displayed, for example. In this case, the display orientation of a graph generated for each index is determined, and the graph is displayed in the determined display orientation.

Furthermore, in the above-described first embodiment, a case has been described in which the arrangement direction of the index values is determined depending on an environment. In addition, the medical information processing apparatus 300 may determine a display orientation in accordance with a different graph to be displayed for comparison. This will be described below.

When the display orientation is determined in accordance with a different graph to be displayed for comparison, the control function 351 acquires a first index value, which is obtained based on fluid analysis that is performed based on an image including a blood vessel of a subject and that is related to blood flow at each of positions in a blood vessel. That is, the control function 351 acquires the index value obtained through the fluid analysis, as one of index values to be displayed for comparison. Here, the control function 351 may acquire, as the first index value, the same index value as the index value described in the first embodiment.

Then, the determination function 353 acquires external information including a second index value related to the blood flow at each of the positions in the blood vessel. For example, the determination function 353 acquires external information including, as the second index value, a measurement result obtained through measurement performed by an FFR measurement apparatus. The determination function 353 may acquire, as the second index value, various index values different from the first index value, rather than the above-described measurement result obtained by the FFR measurement apparatus. For example, the determination function 353 may acquire, as the second index value, a past index value of a subject for whom the first index value has been acquired. Here, for example, the determination function 353 may acquire, as the external information, information on the second index value displayed on a window different from an application of the fluid analysis, information on the second index value displayed by being loaded on the application of the fluid analysis, or information on the second index value displayed on a different apparatus.

Then, the determination function 353 changes one of an arrangement direction of the index values in a first graph, in which the first index value at each of the positions in the long axis direction of the blood vessel is plotted, and an arrangement direction of the index values in a second graph, in which the second index value at each of the positions in the long axis direction of the blood vessel is plotted, in accordance with the other one of the arrangement directions. For example, the determination function 353 changes one of an arrangement direction of the index values in the first graph, in which the first index values obtained based on the fluid analysis are plotted, and an arrangement direction of the index values in the second graph, in which the second index values measured by the FFR measurement apparatus are plotted, in accordance with the other one of the arrangement directions. That is, the determination function 353 determines the display orientation of the graphs such that the arrangement direction of the index values in one of the graphs matches the arrangement direction of the index values in the other one of the graphs.

A case will be described in which a graph of the FFR measured by the FFR measurement apparatus is acquired as the external information. In this case, the determination function 353 may directly acquire a measurement result (the value of the FFR at each of positions in a blood vessel, or a graph) from the FFR measurement apparatus, or indirectly acquires a measurement result that a different apparatus has acquired from the FFR apparatus. Then, the determination function 353 adjusts the arrangement directions of the graphs for displaying the acquired measurement result and the result of the fluid analysis performed by the control function 351 (the graphs of the values of the FFR at the respective positions in the blood vessel). Here, the determination function 353 changes the arrangement direction of the values of the FFR in one of the graph of the FFR obtained by the FFR measurement apparatus and the graph of the FFR obtained through the fluid analysis.

As described above, the display orientation of the graph displayed by the FFR measurement apparatus in the FFR orientation of the graph of the FFR obtained through the fluid analysis. Therefore, the determination function 353 reverses the display orientation of one of the graphs such that the display orientations of both of the graphs (the arrangement directions of the values of the FFR) match each other. FIG. 11A and FIG. 11B are schematic diagrams illustrating examples of a change in the display orientation by the determination function 353 according to the second embodiment. FIG. 11A and FIG. 11B illustrate processes performed by the determination function 353 to display the graph of the FFR obtained by the FFR measurement apparatus in a region R1 and to display the graph of the FFR obtained through the fluid analysis in a region R2.

For example, as illustrated in FIG. 11A, the determination function 353 changes the arrangement direction of the values of the FFR such that the display orientation of the graph of the FFR obtained through the fluid analysis matches the graph of the FFR obtained by the FFR measurement apparatus. That is, as illustrated in the upper section of FIG. 11A, the determination function 353 changes the graph of the FFR obtained through the fluid analysis such that the display orientation matches the graph of the FFR in which the peripheral side is arranged on the left side and the branched side is arranged on the right side. Consequently, the display control function 354 displays a curved line L3 indicating an FFR measurement result obtained by the FFR measurement apparatus and a curved line L4 indicating an FFR analysis result obtained through the fluid analysis in the same display orientation as illustrated in the lower section of FIG. 11A.

For another example, as illustrated in FIG. 11B, the determination function 353 changes the arrangement direction of the values of the FFR such that the display orientation of the graph of the FFR obtained by the FFR measurement apparatus matches the graph of the FFR obtained through the fluid analysis. That is, as illustrated in the upper section of FIG. 11B, the determination function 353 changes the graph of the FFR in which the peripheral side is arranged on the left side and the branched side is arranged on the right side such that the display orientation matches the graph of the FFR obtained through the fluid analysis (the display orientation in which the branched side is arranged on the left side and the peripheral side is arranged on the right side). Consequently, the display control function 354 displays the curved line L3 indicating the FFR measurement result obtained by the FFR measurement apparatus and the curved line L4 indicating the FFR analysis result obtained through the fluid analysis in the same display orientation as illustrated in the lower section of FIG. 11B.

Figure 12:
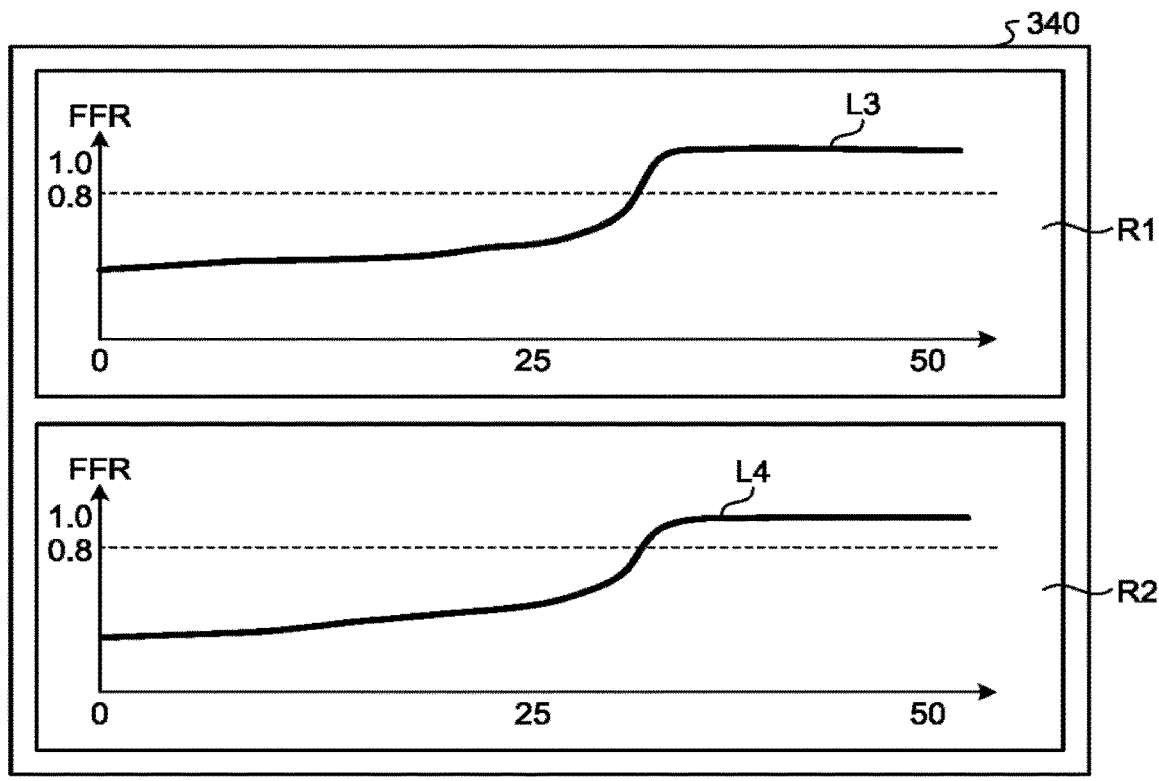
FIG. 12 is a diagram illustrating an example of display of a graph by a display control function according to the second embodiment.

The display control function 354 displays the first graph and the second graph such that the scales of the graphs match each other. Specifically, the display control function 354 displays a plurality of graphs such that the scales of the horizontal axes match each other. The horizontal axis of the graph of the FFR represents a position in a blood vessel, and is indicated by, for example, a distance or the like. FIG. 12 is a diagram illustrating an example of display of a graph by the display control function 354 according to the second embodiment. For example, as illustrated in FIG. 12, the display control function 354 displays the graphs such that the horizontal axis of the graph of the FFR obtained by the FFR measurement apparatus, which is displayed in the region R1, and the horizontal axis of the graph of the FFR obtained through the fluid analysis, which is displayed in the region 2, are adjusted so as to represent a distance of "0 to 52 millimeters (mm)" from a measurement start point at which the measurement using a pressure wire is started.

Furthermore, when a data collection region is different between the first graph and the second graph, it may be possible to omit display of a part of data in the graph corresponding to a larger collection region, in accordance with the graph corresponding to a smaller collection region. For example, when the first graph displays measurement values for a distance of 2 centimeters (cm) from a reference position in a blood vessel, whereas the second graph displays measurement values for a distance of 1.5 cm from the reference position in the blood vessel, it may be possible to omit display of data for 0.5 cm on the peripheral side in the first graph to display the first graph and the second graph such that the display regions match each other.

Here, when the second index value is the measurement result obtained through measurement performed by the FFR measurement apparatus, the display control function 354 can adjust the scale of the graph based on the measurement velocity used by the FFR measurement apparatus. For example, the display control function 354 can calculate a distance from the measurement start point by using an auto pull-back function of the FFR measurement apparatus. In the FFR measurement by the FFR measurement apparatus, it is possible to pull back a pressure wire at a constant velocity, so that it is possible to calculate a distance from the measurement start point based on a time in which the pressure wire is pulled back during the FFR measurement. For example, the display control function 354 calculates distance from the measurement start point to the branched portion based on a time taken to pull back the pressure wire from a predetermined position in the blood vessel (the measurement start point) to the branched portion. Then, the display control function 354 displays, in the region R2, a graph of the values of the FFR from the branched portion to a position at the calculated distance in the blood vessel corresponding to the CT image data used for the fluid analysis. Consequently, the display control function 354 can display the graph of the FFR obtained by the FFR measurement apparatus and the graph of the FFR obtained through the fluid analysis using the CT image data such that the scales of the graphs match each other.

The scales of the graphs may be adjusted by other methods, instead of the above-described method. For example, the display control function 354 displays a CT image generated from the CT image data used for the fluid analysis and accepts an operation of specifying a position in the CT image at which the FFR is measured using a pressure wire, to thereby acquire information on a blood vessel region measured by the FFR measurement apparatus. Then, the display control function 354 displays, in the region R2, a graph of the values of the FFR in the acquired blood vessel region in the blood vessel corresponding to the CT image data used for the fluid analysis.

Figure 13:
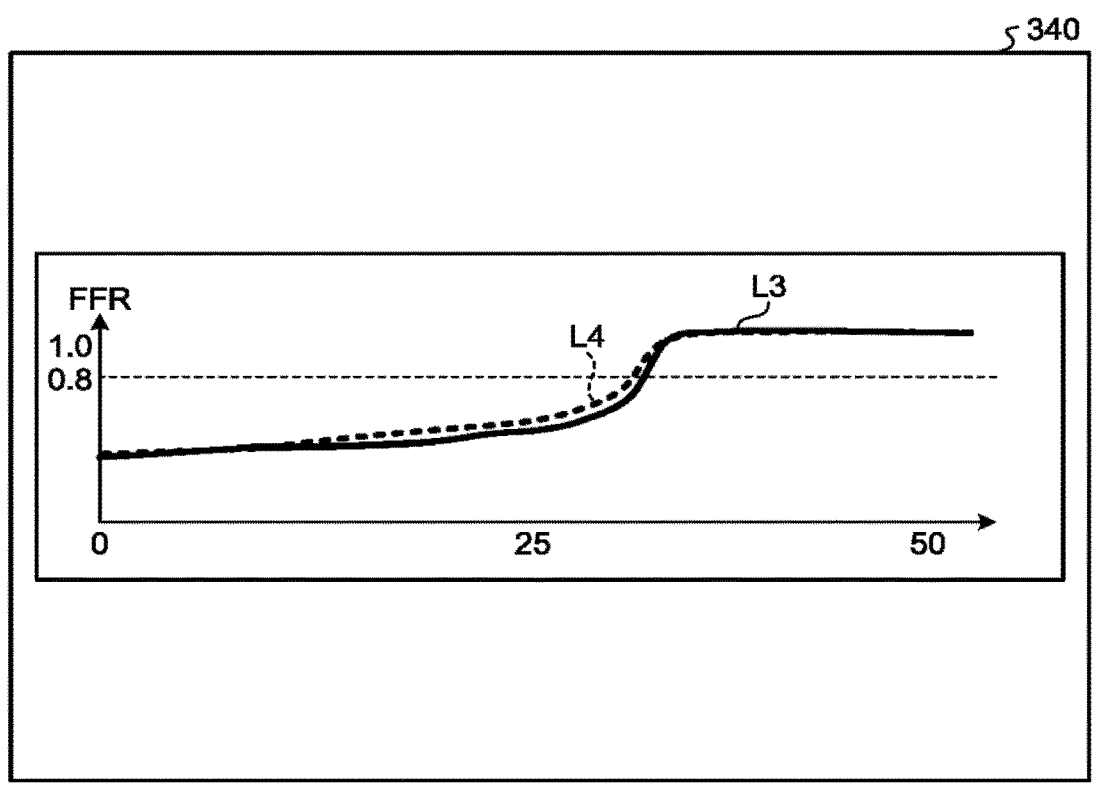
FIG. 13 is a diagram illustrating an example of display of a graph by the display control function according to the second embodiment.

Furthermore, the display control function 354 may adjust the scales of graphs and display the graphs in an overlapping manner. FIG. 13 is a diagram illustrating an example of display of a graph by the display control function 354 according to the second embodiment. For example, as illustrated in FIG. 13, the display control function 354 can display, on a single graph, the curved line L3 indicating the FFR measurement result obtained by the FFR measurement apparatus and the curved line L4 indicating the FFR analysis result obtained through the fluid analysis. In this case, as illustrated in FIG. 13, the display control function 354 may display each of the curved lines in a distinguishable manner. For example, the display control function 354 may display the curved lines in a distinguishable manner by displaying the curved line L4 indicating the FFR analysis result obtained through the fluid analysis in a color that is not used for the FFR measurement result obtained by the FFR measurement apparatus.

Figure 14:
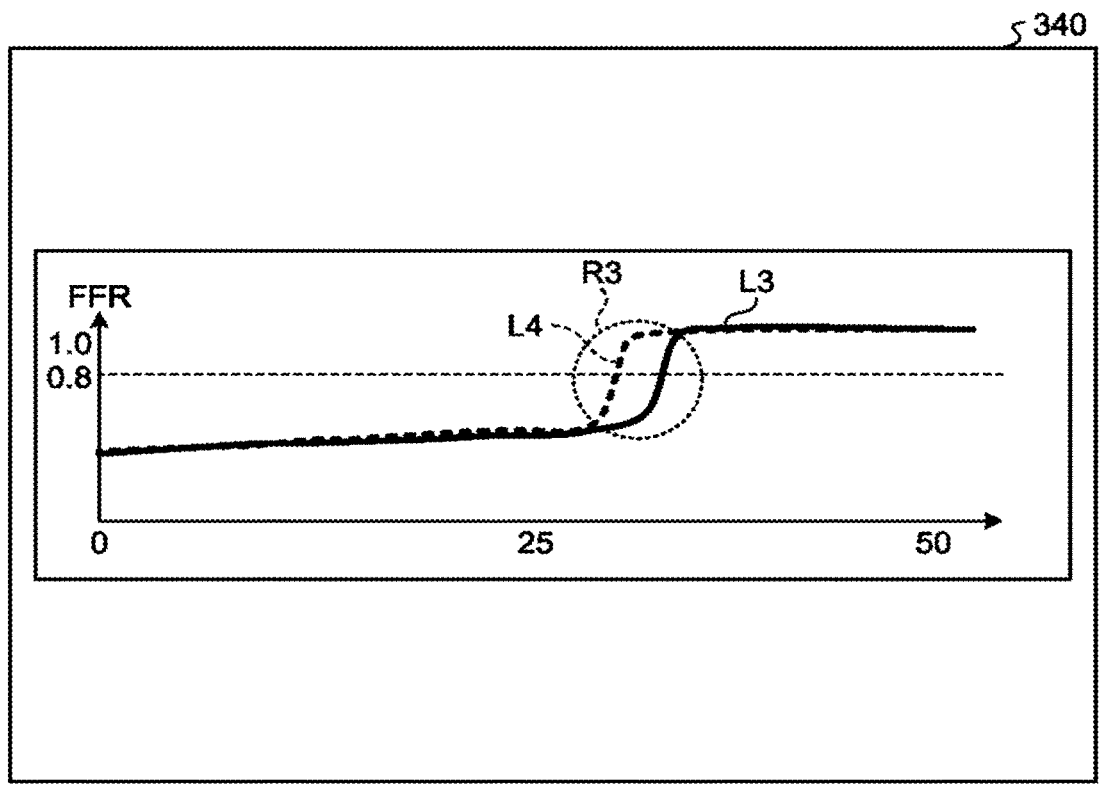
FIG. 14 is a diagram for explaining an example of display by the display control function according to the second embodiment.

Furthermore, the display control function 354 may display, in an intensified manner, a portion in which results in a plurality of graphs are different. For example, the display control function 354 displays, in an intensified manner, a portion in which a difference between the first graph and the second graph exceeds a predetermined threshold. FIG. 14 is a diagram for explaining an example of display by the display control function 354 according to the second embodiment. For example, as illustrated in a region R3 in FIG. 14, the display control function 354 displays, in an intensified manner, a portion in which the position at which the value of the FFR largely changes in the curved line L3 is largely deviated from the curved line 54. In this case, the display control function 354 calculates a distance between the position at which the FFR value largely changes in the curved line L3 and the position at which the FFR value largely changes in the curved line L4, and displays a corresponding portion in an intensified manner when the calculated distance exceeds a predetermined threshold.

The portion displayed in the intensified manner by the display control function 354 is not limited to the above-described example, and other portions may be displayed in an intensified manner. For example, the display control function 354 may display, in an intensified manner, a portion in which the values of the FFR at the same position in the curved line L3 and the curved line L4 are largely different. In this case, the display control function 354 obtains a difference between the the value of the FFR indicated by the curved line L3 and the value of the FFR indicated by the curved line L4, and displays a corresponding portion in an intensified manner when the value of the difference exceeds a predetermined threshold.

Figure 15:
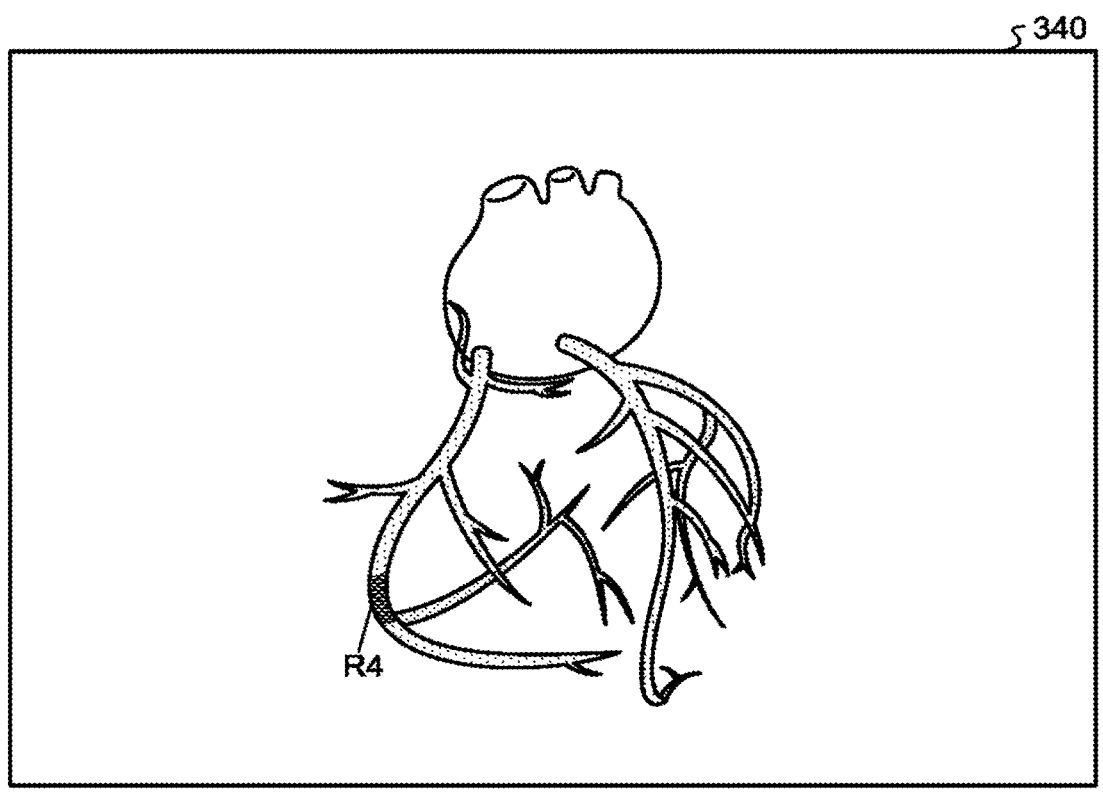
FIG. 15 is a diagram illustrating an example of display by the display control function according to the second embodiment.

Furthermore, the display control function 354 may present a position on an image corresponding to a portion in which results in a plurality of graphs are different. Specifically, the display control function 354 displays a blood vessel image, in which a blood vessel region corresponding to a portion in which a difference between the first graph and the second graph exceeds a predetermined threshold is intensified. FIG. 15 is a diagram illustrating an example of display by the display control function 354 according to the second embodiment. For example, as illustrated in FIG. 15, the display control function 354 displays, in an intensified manner, a region R4 in which results in a plurality of graphs are different in a three-dimensional (3D) model generated based on the CT image data used for the fluid analysis. The region of the CT image data in which the results in the plurality of graphs are different can be identified based on a position in the blood vessel in which results obtained by calculating differences between the graphs are different.

In FIG. 15, a case has been illustrated in which the 3D model generated based on the CT image data is used; however, the embodiment is not limited to this example. For example, it may be possible to use a CT image generated from the CT image data. In this case, the display control function 354 displays a region, in which the results in the plurality of graphs are different, in an intensified manner in the CT image. Furthermore, in FIG. 15, a case has been illustrated in which only the blood vessel image (a 3D model or a CT image) is displayed; however, the embodiment is not limited to this example. It may be possible to display a graph together with the blood vessel image.

The FFR measurement result obtained by the FFR measurement apparatus explained in the above-described embodiments may be a result obtained before an operation or a result obtained after an operation. That is, the determination function 353 may acquire the measurement result obtained through measurement performed by the FFR measurement apparatus before an operation is performed on a subject, or may acquire external information including, as the second index value, the measurement result obtained through measurement performed by the FFR measurement apparatus after an operation is performed on the subject.

Furthermore, in the above-described embodiments, a case has been described in which the graph of the FFR obtained by the FFR measurement apparatus and the graph of the FFR obtained through the fluid analysis using the CT image data are compared. However, the embodiment is not limited to this example. For example, it may be possible to display a graph of an FFR obtained through past fluid analysis and a graph of an FFR obtained through current fluid analysis in a comparable manner. As one example, when the graph obtained through the fluid analysis performed in the past is recorded in a medical record in the same display orientation as the graph of the FFR obtained by the FFR measurement apparatus, the determination function 353 may change a display orientation of the graph of the FFR obtained through the current fluid analysis (the arrangement direction of the values of the FFR) to the same orientation as the graph of the FFR recorded in the medical record. Consequently, the display control function 354 displays the graphs of the analysis results obtained through the past fluid analysis and the current fluid analysis in the same display orientation (the arrangement direction of the values of the FFR) as the graph of the FFR obtained by the FFR measurement apparatus.

Similarly, when a graph, which is obtained in the past by the FFR measurement apparatus, is recorded in a medical record in the same orientation as the graph of the FFR obtained through the fluid analysis, the determination function 353 may change the display orientation of a graph of an FFR currently obtained by the FFR measurement apparatus (the arrangement direction of the values of the FFR) to the same orientation as the graph of the FFR recorded in the medical record. Consequently, the display control function 354 displays the graphs of the past measurement result and the current measurement result obtained by the FFR measurement apparatus in the same display orientation (the arrangement direction of the values of the FFR) as the graph of the FFR obtained through the fluid analysis.

Furthermore, in the above-described embodiments, a case has been described in which two graphs are displayed for comparison. However, the embodiments are not limited to this example. It may be possible to display three or more graphs in a comparable manner.

In the above-described embodiments, a case has been described in which a single processing circuitry (the processing circuitry 350) implements various processing functions; however, the embodiments are not limited to this example. The processing circuitry 350 may be configured by a combination of a plurality of independent processors, and causes each of the processor to execute each of programs to implement each of the processing functions. In addition, the processing functions included in the processing circuitry 350 may be appropriately distributed or integrated, and may be implemented by a single processing circuitry or a plurality of processing circuitries.

Furthermore, the term "processor" used in the above-described embodiments means, for example, a central processing unit (CPU), a graphics processing unit (CPU), or a circuitry, such as an application specific integrated circuit (ASIC) or a programmable logic device (for example, a simple programmable logic device (SPLD), a complex programmable logic device (CPLD), or a field programmable gate array (FPGA)). It may be possible to directly incorporate a program in the circuitry of the processor, instead of storing the program in the memory. In this case, the processor reads and executes the program incorporated in the circuitry to implement the functions. Furthermore, each of the processors according to the embodiments does not necessarily have to be configured as a single circuitry, but may be configured as a single processor by a combination of a plurality of independent circuitries to implement the functions.

The program executed by the processor is provided by being incorporated in a read only memory (ROM), a memory, or the like in advance. The program may be provided by being recorded in a computer-readable recording medium, such as a compact disk-ROM (CD-ROM), a flexible disk (FD), a CD-recordable (CD-R), or a digital versatile disk (DVD), in a file format installable or executable by the apparatus. Furthermore, the program may be stored in a computer connected to a network, such as the Internet, and may be provided or distributed by being downloaded via the network. For example, the program is configured by modules including respective functional units. As actual hardware, the CPU reads the program from a storage medium, such as a ROM, and executes the program, so that each of the modules are loaded on a main storage device and generated on the main storage device.

According to at least one of the above-described embodiments, it is possible to improve the visibility of a graph of an index related to blood flow.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus comprising:

processing circuitry configured to:
acquire a first index value obtained based on fluid analysis that is performed based on an image including a first region of a blood vessel of a subject, the first index value being related to blood flow at each of positions in the first region of the blood vessel,
acquire clinical information of the subject from an external apparatus,
judge whether the clinical information is a second index value obtained by inserting a pressure wire into a second region of the blood vessel of the subject and measuring a pressure, the second region of the blood vessel including at least a part of the first region of the blood vessel, the second index value being related to blood flow at each of the positions in the second region of the blood vessel, output a display control signal, when the clinical information is the second index value obtained by inserting a pressure wire into the second region of the blood vessel of the subject and measuring a pressure, display a first graph and a second graph on a display, the first graph being a graph in which the first index value at each of positions in a long axis direction of the blood vessel is plotted, and the second graph being a graph in which the second index value at each of the positions in the long axis direction of the blood vessel is plotted, and control, in accordance with reception of the display control signal, the display of the first graph and the second graph on the display such that the directions of the first and second graphs match each other.

2. The medical information processing apparatus according to claim 1, wherein the processing circuitry is configured to change the direction of the long axis to match a direction of the long axis of the first graph with a direction of the long axis of the second graph.

3. The medical information processing apparatus according to claim 1, wherein the processing circuitry is configured to acquire, as the second index value, a measurement result obtained through measurement performed by a fractional flow reserve (FFR) measurement apparatus; and change one of an arrangement direction of index values in a first graph and an arrangement direction of index values in a second graph in accordance with the other one of the arrangement directions, the first graph being a graph in which the first index values obtained based on the fluid analysis are plotted, and the second graph being a graph in which the second index values measured by the FFR measurement apparatus are plotted.

4. The medical information processing apparatus according to claim 3, wherein the processing circuitry is configured to acquire, as the second index value, one of a measurement result obtained through measurement performed by the FFR measurement apparatus before an operation is performed on a subject and a measurement result obtained through measurement performed by the FFR measurement apparatus after an operation is performed on the subject.

5. The medical information processing apparatus according to claim 3, wherein the change of the direction of the long axis is reversing the axis.

6. The medical information processing apparatus according to claim 1, wherein the processing circuitry is configured to display the first graph and the second graph such that scales of the graphs match each other.

7. The medical information processing apparatus according to claim 6, wherein the processing circuitry is configured to display the first graph and the second graph in an overlapping manner.

8. The medical information processing apparatus according to claim 6, wherein the processing circuitry is configured to display the first graph and the second graph in a distinguishable manner.

9. The medical information processing apparatus according to claim 6, wherein the processing circuitry is configured to display, in an intensified manner, a portion in which a difference between the first graph and the second graph exceeds a predetermined threshold.

10. The medical information processing apparatus according to claim 6, wherein the processing circuitry is configured to display a blood vessel image in which a blood vessel region corresponding to a portion in which a difference between the first graph and the second graph exceeds a predetermined threshold is intensified.

11. The medical information processing apparatus according to claim 6, wherein the processing circuitry is configured to, when the second index value is the measurement result obtained through measurement performed by a fractional flow reserve (FFR) measurement apparatus, acquire information on each position of the blood vessel for which the second index value has been obtained based on a moving velocity of the pressure wire used by the FFR measurement apparatus and adjust scales of the graphs based on the information on each position of the blood vessel.

12. A medical information processing method comprising:

acquiring a first index value obtained based on fluid analysis that is performed based on an image including a first region of a blood vessel of a subject, the first index value being related to blood flow at each of positions in the first region of the blood vessel;

acquiring clinical information of the subject from an external apparatus;

judging whether the clinical information is a second index value obtained by inserting a pressure wire into a second region of the blood vessel of the subject and measuring a pressure, the second region of the blood vessel including at least a part of the first region of the blood vessel, the second index value being related to blood flow at each of the positions in the second region of the blood vessel;

outputting a display control signal, when the clinical information is the second index value obtained by inserting a pressure wire into the second region of the blood vessel of the subject and measuring a pressure;

displaying a first graph and a second graph on a display, the first graph being a graph in which the first index value at each of positions in a long axis direction of the blood vessel is plotted, and the second graph being a graph in which the second index value at each of the positions in the long axis direction of the blood vessel is plotted; and controlling, in accordance with reception of the display control signal, the display of the first graph and the second graph on the display such that the directions of the first and second graphs match each other.

13. A medical information processing system including a fluid analysis apparatus configured to perform fluid analysis on an image including a blood vessel, an external apparatus configured to acquire clinical information and a display apparatus, wherein the display apparatus comprising:

processing circuitry configured to:

acquire a first index value obtained based on fluid analysis that is performed based on an image including a first region of a blood vessel of a subject from the fluid analysis apparatus, the first index value being related to blood flow at each of positions in the first region of the blood vessel, acquire clinical information of the subject from the external apparatus, judge whether the clinical information is a second index value obtained by inserting a pressure wire into a second region of the blood vessel of the subject and measuring a pressure, the second region of the blood vessel including at least a part of the first region of the blood vessel, the second index value being related to blood flow at each of the positions in the second region of the blood vessel, output a display control signal, when the clinical information is the second index value obtained by inserting a pressure wire into the second region of the blood vessel of the subject and measuring a pressure, display a first graph and a second graph on a display, the first graph being a graph in which the first index value at each of positions in a long axis direction of the blood vessel is plotted, and the second graph being a graph in which the second index value at each of the positions in the long axis direction of the blood vessel is plotted, and control, in accordance with reception of the display control signal, the display of the first graph and the second graph on the display such that the directions of the first and second graphs match each other.

* * * * *